US012673956B2

(12) United States Patent
Beresis et al.

(10) Patent No.: US 12,673,956 B2
(45) Date of Patent: Jul. 7, 2026

(54) OXADIAZOLYL DIHYDROPYRANO[2,3-B]PYRIDINE INHIBITORS OF HIPK2 FOR TREATING KIDNEY FIBROSIS

(71) Applicants: ICAHN SCHOOL OF MEDICINE AT MOUNT SINAI, New York, NY (US); THE UNITED STATES GOVERNMENT AS REPRESENTED BY THE DEPARTMENT OF VETERANS AFFAIRS, Washington, DC (US)

(72) Inventors: Richard T. Beresis, San Francisco, CA (US); John Cijiang He, Forest Hills, NY (US); Kyung Lee, Bronx, NY (US)

(73) Assignees: Icahn School of Medicine at Mount Sinai, New York, NY (US); The United States Government as Represented by the Department of Veterans Affairs, Washington, DC (US)

(*) Notice: Subject to any disclaimer, the term of this patent is extended or adjusted under 35 U.S.C. 154(b) by 300 days.

(21) Appl. No.: 18/264,809

(22) PCT Filed: Feb. 9, 2022

(86) PCT No.: PCT/US2022/015767

§ 371 (c)(1),
(2) Date: Aug. 9, 2023

(87) PCT Pub. No.: WO2022/173795

PCT Pub. Date: Aug. 18, 2022

(65) Prior Publication Data

US 2025/0179084 A1 Jun. 5, 2025

Related U.S. Application Data

(60) Provisional application No. 63/147,859, filed on Feb. 10, 2021.

(51) Int. Cl.

| | |
|---|---|
| ***C07D 491/052*** | (2006.01) |
| ***A61K 31/436*** | (2006.01) |
| ***A61P 13/12*** | (2006.01) |

(52) U.S. Cl.
CPC ........ *C07D 491/052* (2013.01); *A61K 31/436* (2013.01); *A61P 13/12* (2018.01)

(58) Field of Classification Search
CPC ........ C07D 491/052; A61P 13/12; A61P 1/16; A61P 9/00; A61P 11/00; A61K 31/436
See application file for complete search history.

(56) References Cited

U.S. PATENT DOCUMENTS

| | | | |
|---|---|---|---|
| 10,669,266 | B2 | 6/2020 | He et al. |
| 2010/0168005 | A1 | 7/2010 | Bolli et al. |
| 2010/0174065 | A1 | 7/2010 | Heer et al. |
| 2011/0274657 | A1 | 11/2011 | Izquierdo et al. |
| 2019/0352292 | A1 | 11/2019 | He et al. |

FOREIGN PATENT DOCUMENTS

| | | | |
|---|---|---|---|
| WO | 2018231745 | A1 | 12/2018 |
| WO | 2022173795 | A1 | 8/2022 |

OTHER PUBLICATIONS

Siani, "Pharmacological Treatment of Fibrosis: a Systematic Review of Clinical Trials", SN Comprehensive Clinical Medicine, (2020) 2, pp. 531-550 (Year: 2020).*
Pubchem, Substance Record for SID 379155454, Modify Date: Jun. 3, 2019 [retrieved on Oct. 18, 2023]. Retrieved from the Internet: <URL: https://pubchem.ncbi.nlm.nih.gov/substance/379155454>.
International Search Report and Written Opinion issued in PCT/US2022/015767 and mailed May 17, 2022.

* cited by examiner

*Primary Examiner* — Sahar Javanmard
(74) *Attorney, Agent, or Firm* — Heslin Rothenberg Farley & Mesiti P.C.

(57) ABSTRACT

Compounds that are selective inhibitors of Smad3 activation are disclosed. The compounds are (3-aryl-1,2,4-oxadiazol-5-yl)-3,4-dihydro-2H-pyrano[2,3-b]pyridines of the following structure:

I

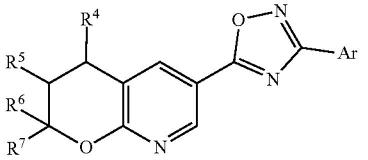

in which Ar is aryl or heteroaryl. The compounds disclosed are useful in treatment of fibrotic disease, particularly renal fibrosis, and similar diseases associated with the dysregulation of the HIPK2/Smad3 signaling pathway.

18 Claims, No Drawings

OXADIAZOLYL DIHYDROPYRANO[2,3-B]PYRIDINE INHIBITORS OF HIPK2 FOR TREATING KIDNEY FIBROSIS

CROSS-REFERENCE TO RELATED APPLICATION

This application claims priority of U.S. provisional application 63/147,859, filed Feb. 10, 2021, the entire disclosure of which is hereby incorporated herein by reference.

FIELD OF THE INVENTION

This invention relates to oxadiazolyl dihydropyrano[2,3-b]pyridine inhibitors of homeodomain interacting protein kinase 2 (HIPK2). The compounds disclosed are useful in treatment of fibrotic diseases, particularly kidney fibrosis.

BACKGROUND

Fibrosis is characterized by excessive production and accumulation of extracellular matrix proteins, which leads to progressive loss of tissue function and eventual organ failure. Chronic kidney diseases, irrespective of primary insults, are usually accompanied by kidney interstitial fibrosis. Therapeutic strategy for chronic kidney disease, in order to halt decline of kidney function, requires not only removal of the causal factors, such as hyperglycemia, hypertension, and HIV infection, but also anti-fibrosis therapy to restore the normal kidney structure and function. A number of other organ-specific fibrotic disorders are known, in addition to kidney fibrosis, including liver, cardiac and pulmonary fibrosis.

Renal fibrosis is considered the final convergent pathway for progressive chronic kidney disease, regardless of the original etiologies of the disease. Although much has been learned of the molecular mechanisms underlying renal fibrogenesis, there is still a paucity of success in translating this knowledge to clinical application. It has been demonstrated that HIPK2 is a multifunctional activator of TGF-β/Smad3, NF-κB, and p53 pathways and that the global knockout of HIPK2 in mice attenuated kidney fibrosis in vivo. U.S. Pat. No. 10,669,266 discloses small molecule inhibitors of HIPK2 that specifically block TGF-β/Smad3 pathway to attenuate renal fibrosis without causing adverse systemic effects. However, solubility and potency issues remain with the compounds disclosed in the '266 patent.

Transforming growth factor-β1 (TGF-β1) has been identified to be the most important pro-fibrogenic factor for kidney disease. TGF-β1 binds to type II TGF-β receptor, allowing its dimerization with type I TGF-β receptor and leading to phosphorylation of Smad2 and Smad3. Phosphorylated Smad3 relocates into nuclei, thereby binds to Smad binding element in promoter and activating the transcription of the target genes including pro-fibrotic genes such as collagen I, fibronectin, and alpha-smooth muscle actin (α-SMA). It is known that Smad3 is highly activated in fibrotic kidney and that knockout of Smad3 attenuates kidney fibrosis in animal models of kidney disease. Blockade of TGF-β1/Smad3 pathway therefore provides a therapeutic strategy for kidney fibrosis.

BRIEF SUMMARY OF THE INVENTION

It has now been found that certain compounds described below selectively inhibit Smad3 activation.

In one aspect, the invention relates to compounds of general formula I

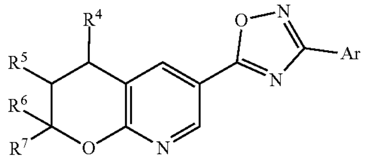

I wherein

Ar is (a) phenyl substituted at the meta and/or para positions with one or more substituents chosen independently from hydrogen, —$(C_1\text{-}C_8)$hydrocarbyl, OH, —$O(C_1\text{-}C_8)$hydrocarbyl, halogen, nitro, amino, $(C_1\text{-}C_3)$alkylamino, $(C_1\text{-}C_3)$dialkylamino, $(C_1\text{-}C_3)$acylamino, $(C_1\text{-}C_3)$alkylsulfonyl, $(C_1\text{-}C_3)$haloalkyl, $(C_1\text{-}C_3)$haloalkoxy, 5- or 6-membered heterocyclyl, and —$B(OH)_2$; or (b) 5-membered heteroaryl substituted with one substituent chosen from hydrogen, —$(C_1\text{-}C_3)$alkyl, OH, —$O(C_1\text{-}C_3)$alkyl, halogen, amino, $(C_1\text{-}C_3)$alkylamino, $(C_1\text{-}C_3)$dialkylamino, $(C_1\text{-}C_3)$haloalkyl, and $(C_1\text{-}C_3)$haloalkoxy;

$R^4$ is chosen from hydrogen, hydroxy, $(C_1\text{-}C_3)$alkyl, $(C_1\text{-}C_3)$alkoxy, amino, $(C_1\text{-}C_3)$alkylamino, and $(C_1\text{-}C_3)$dialkylamino;

$R^5$ is chosen from hydrogen, hydroxy, $(C_1\text{-}C_3)$alkyl, $(C_1\text{-}C_3)$alkoxy, amino, $(C_1\text{-}C_3)$alkylamino, and $(C_1\text{-}C_3)$dialkylamino;

$R^6$ is chosen from hydrogen and $(C_1\text{-}C_6)$hydrocarbyl; and $R^7$ is chosen from hydrogen and $(C_1\text{-}C_3)$alkyl;

with the proviso that not all of $R^4$, $R^5$, $R^6$, and $R^7$ are hydrogen.

In another aspect, the invention relates to pharmaceutical compositions comprising a pharmaceutically acceptable carrier and a compound of formula I.

In another aspect, the invention relates to methods for inhibiting the interaction of homeodomain interacting protein kinase 2 (HIPK2) with Smad3. The method comprises bringing HIPK2 into contact with a compound of formula I.

In another aspect, the invention relates to methods for inhibiting Smad3 activation. The method comprises bringing Smad3 into contact with a compound of formula I.

In another aspect, the invention relates to a method for treating a fibrotic disease comprising administering a compound of formula I.

DETAILED DESCRIPTION OF THE INVENTION

In one aspect, the invention relates to compounds having general formula I as described above:

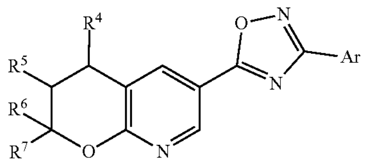

I

In some embodiments of formula I, Ar is phenyl. In some embodiments, the phenyl may be para-substituted with a substituent chosen from bromo, chloro, fluoro, fluoromethyl, difluoromethyl, trifluoromethyl, methyl, oxetanyl, and —$B(OH)_2$. The phenyl may be substituted with other substituents in addition to the one at the para position.

In some embodiments, Ar is a 5-membered heteroaryl. In some embodiments the 5-membered heteroaryl is chosen from oxazole, thiophene, pyrazole, and thiazole, which may be unsubstituted or substituted with a substituent chosen from —($C_1$-$C_3$)hydrocarbyl, bromo, chloro, fluoro, fluoromethyl, difluoromethyl, and trifluoromethyl. In some embodiments, Ar is thiazol-2-yl substituted at 3- or 4-with chloro or methyl.

In some embodiments of formula I, $R^4$ is chosen from hydrogen, hydroxy and amino. In some embodiments, $R^5$ is chosen from hydrogen, hydroxy and amino. In some embodiments, $R^6$ and $R^7$ are independently chosen from hydrogen and methyl. In a particular embodiment, Ar is chlorophenyl, $R^4$ is hydrogen, $R^5$ is hydroxyl and both of $R^6$ and $R^7$ are methyl. In another particular embodiment, Ar is chlorophenyl, $R^4$ is hydroxyl, $R^5$ is hydrogen, and both of $R^6$ and $R^7$ are methyl.

For convenience and clarity, certain terms employed in the specification, examples, and claims are described herein. Substituents $R^n$ are generally defined when introduced and retain that definition throughout the specification and in all independent claims.

Unless otherwise specified, alkyl (or alkylene) is intended to include linear or branched saturated hydrocarbon structures and combinations thereof. Alkyl refers to alkyl groups of from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include c-propyl, c-butyl, c-pentyl, norbornyl and the like.

Hydrocarbon or hydrocarbyl includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbon or hydrocarbyl refer to any substituent comprised of hydrogen and carbon as the only elemental constituents. Aliphatic hydrocarbons or hydrocarbyls are hydrocarbons or hydrocarbyls that are not aromatic; they may be saturated or unsaturated, cyclic, linear or branched. Examples of aliphatic hydrocarbons or hydrocarbyls include isopropyl, 2-butenyl, 2-butynyl, cyclopentyl, norbornyl, etc. Aromatic hydrocarbons or hydrocarbyls include benzene (phenyl), naphthalene (naphthyl), anthracene, etc.

Oxaalkyl refers to alkyl residues in which one or more carbons (and their associated hydrogens) have been replaced by oxygen. Examples include methoxy, ethoxy, propoxy, isopropoxy, methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e., it refers to compounds in which the oxygen is bonded via a single bond to its adjacent atoms (forming ether bonds); it does not refer to doubly bonded oxygen, as would be found in carbonyl groups. Alkoxy is a subset of oxaalkyl and includes groups of a straight or branched configuration. Examples include methoxy, ethoxy, propoxy, isopropoxy and the like. Lower-alkoxy refers to groups containing one to four carbons.

In some embodiments, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine. Such compounds (e.g.perfluoroalkyl) fall within the class of "halohydrocarbon" and "haloalkyl".

The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, and as would be understood by the person of skill in the art, the recitation of "a compound"—unless expressly further limited—is intended to include salts of that compound. Thus, for example, the recitation "a compound of formula I" as depicted above would include salts of the (3-aryl-1,2,4-oxadiazol-5-yl)-3,4-dihydro-2H-pyrano[2,3-b]pyridine:

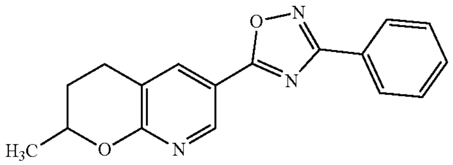

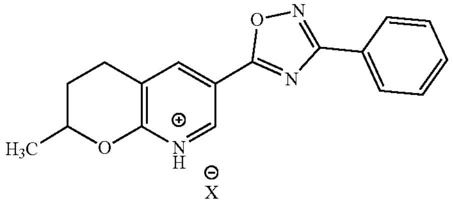

wherein X is a counterion, preferably a pharmaceutically acceptable anion. In a particular embodiment, the term "compound of formula I" refers to the compound or a pharmaceutically acceptable salt thereof.

The term "pharmaceutically acceptable salt" refers to salts whose counter ion derives from pharmaceutically acceptable non-toxic acids and bases. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

A "therapeutically effective amount" means the amount that, when administered to a subject for treating a disorder or condition, is sufficient to effect such treatment.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^{2}H$, $^{3}H$, $^{11}C$, $^{13}C$, $^{14}C$, $^{15}N$, $^{35}S$, $^{18}F$, $^{36}Cl$, $^{125}I$, $^{124}I$ and $^{131}I$ respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formula I of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Persons of skill will readily appreciate that compounds described herein, when appropriately labeled as described above, can be employed in a method of identifying (i.e. labeling) HIPK2. Using methods well known to persons of skill in the art, HIPK2 can be localized in tissues, cells and organelles.

While it may be possible for the compounds of formula I to be administered as the raw chemical, it is preferable to present them as a pharmaceutical composition. According to a further aspect, the present invention provides a pharmaceutical composition comprising a compound of formula I, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining a therapeutic benefit in the form of eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. The compositions may be administered to a patient at risk of developing a particular disease, or to a patient reporting one or more of the physiological symptoms of a disease, even though a diagnosis of this disease may not have been made.

Terminology related to "protecting", "deprotecting" and "protected" functionalities may occur in this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction scheme as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art.

Specific examples of compounds of the present invention made via the schemes above and their test results in the luciferase screen described below are shown in Table 1:
TABLE 1
| Example # | Structure | Luciferase IC50 nM | ID NUMBER SMS21032-0 |
|---|---|---|---|
| 1 | 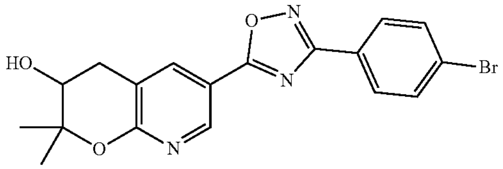 [SMILES: CC1(C)Oc2ncc(-c3nc(-c4ccc(Br)cc4)no3)cc2CC1O] | 43 | 097 |
| 2 | 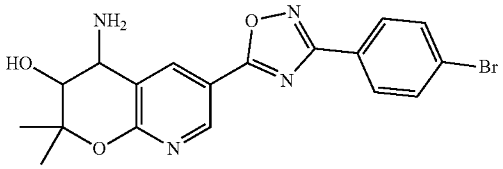 [SMILES: CC1(C)Oc2ncc(-c3nc(-c4ccc(Br)cc4)no3)cc2C(N)C1O] | 8147 | 098 |
| 3 | 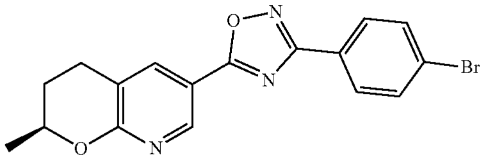 [SMILES: C[C@H]1CCc2cc(-c3nc(-c4ccc(Br)cc4)no3)cnc2O1] | 234 | 130 |
| 4 | 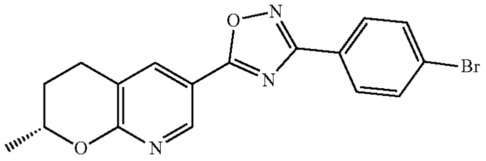 [SMILES: C[C@@H]1CCc2cc(-c3nc(-c4ccc(Br)cc4)no3)cnc2O1] | 126 | 131 |
| 5 | 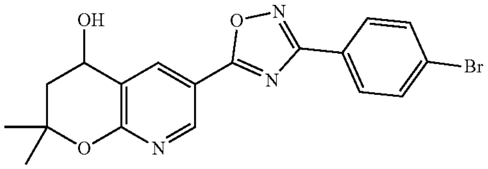 [SMILES: CC1(C)CC(O)c2cc(-c3nc(-c4ccc(Br)cc4)no3)cnc2O1] | 86 | 143 |
| 6 | 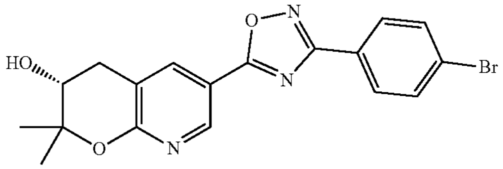 | 27 | 151 |
| 7 | 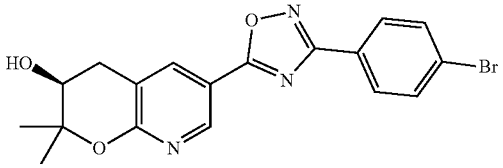 [SMILES: CC1(C)Oc2ncc(-c3nc(-c4ccc(Br)cc4)no3)cc2C[C@@H]1O] | 37 | 152 |
| 8 | 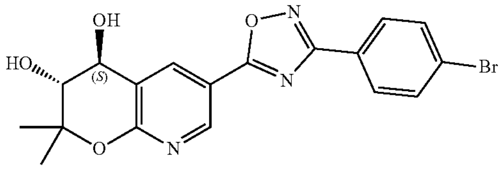 | 11298 | 164 |

TABLE 1-continued
| Example # | Structure | Luciferase IC50 nM | ID NUMBER SMS21032-0 |
|---|---|---|---|
| 9 | 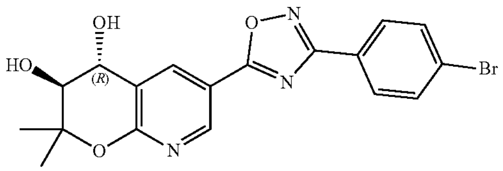 | 2421 | 165 |
| 10 | 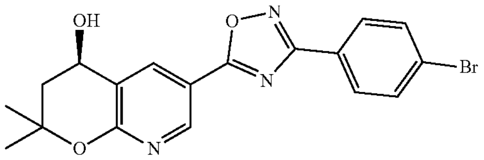 [SMILES: CC1(C)C[C@@H](O)c2cc(-c3nc(-c4ccc(Br)cc4)no3)cnc2O1] | 233 | 171 |
| 11 | 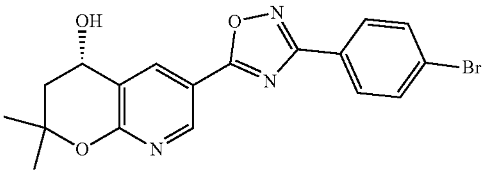 [SMILES: CC1(C)C[C@H](O)c2cc(-c3nc(-c4ccc(Br)cc4)no3)cnc2O1] | 57 | 172 |
| 12 | 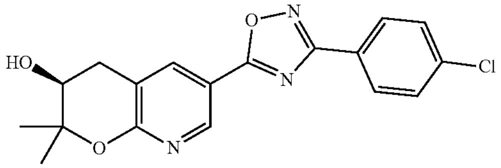 [SMILES: CC1(C)Oc2ncc(-c3nc(-c4ccc(Cl)cc4)no3)cc2C[C@@H]1O] | 89 | 173 |
| 13 | 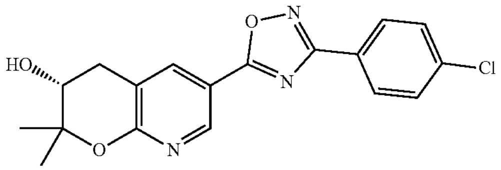 [SMILES: CC1(C)Oc2ncc(-c3nc(-c4ccc(Cl)cc4)no3)cc2C[C@H]1O] | 156 | 174 |
| 14 | 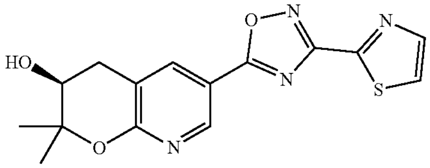 [SMILES: CC1(C)Oc2ncc(-c3nc(-c4nccs4)no3)cc2C[C@@H]1O] | 1374 | 182 |
| 16 | 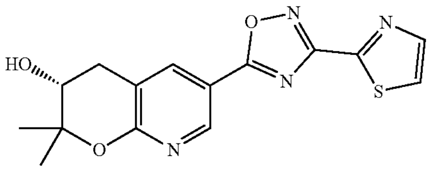 [SMILES: CC1(C)Oc2ncc(-c3nc(-c4nccs4)no3)cc2C[C@H]1O] | 1112 | 183 |
| 17 | 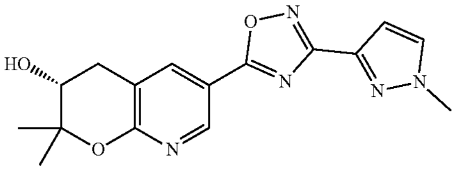 | 18 | 184 |

TABLE 1-continued
| Example # | Structure | Luciferase IC50 nM | ID NUMBER SMS21032-0 |
|---|---|---|---|
| 18 | 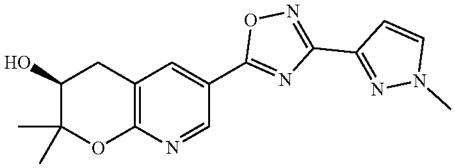 | 28 | 185 |
| 19 | 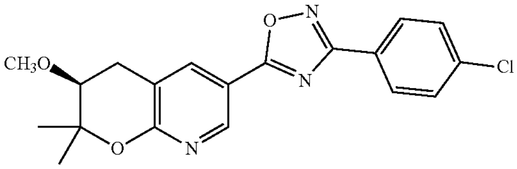 | 340 | 187 |
| 20 | 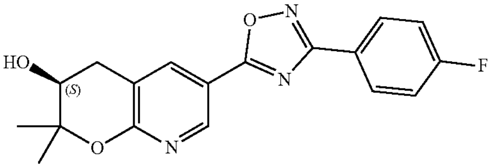 | 223 | 190 |
| 21 | 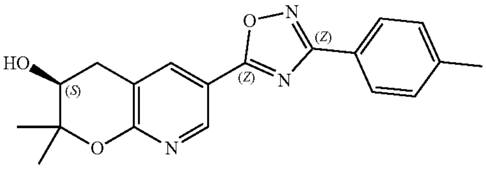 | 17 | 191 |
| 22 | 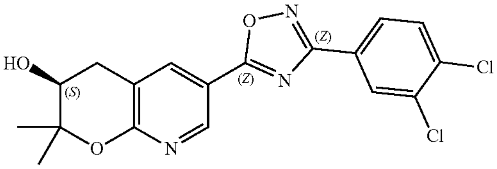 | 43 | 192 |
| 23 | 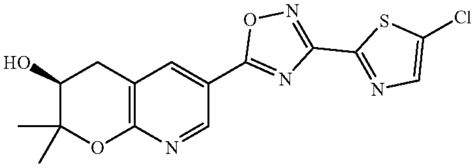 [SMILES: CC1(C)Oc2ncc(-c3nc(-c4ncc(Cl)s4)no3)cc2C[C@@H]1O] | 242 | 193 |
| 24 | 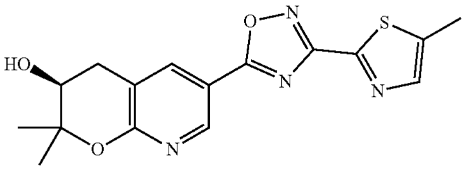 | 822 | 194 |
| 25 | 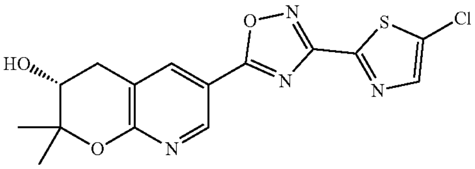 [SMILES: CC1(C)Oc2ncc(-c3nc(-c4ncc(Cl)s4)no3)cc2C[C@H]1O] | 206 | 197 |

TABLE 1-continued
| Example # | Structure | Luciferase IC50 nM | ID NUMBER SMS21032-0 |
| --- | --- | --- | --- |
| 26 | 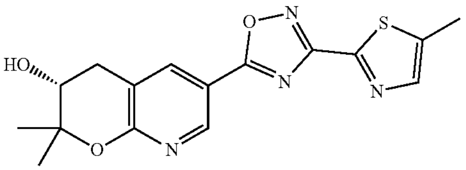 | 708 | 198 |
| 27 | 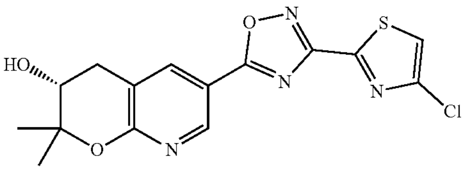 [SMILES: CC1(C)Oc2ncc(-c3nc(-c4nc(Cl)cs4)no3)cc2C[C@H]1O] | 705 | 199 |
| 28 | 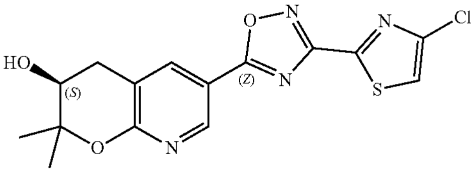 | 13 | 200 |
| 29 | 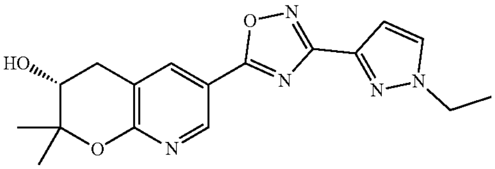 [SMILES: CCn1ccc(-c2noc(-c3cnc4c(c3)C[C@@H](O)C(C)(C)O4)n2)n1] | 56 | 201 |
| 30 | 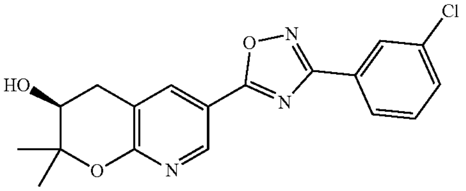 [SMILES: CC1(C)Oc2ncc(-c3nc(-c4cccc(Cl)c4)no3)cc2C[C@@H]1O] | 136 | 211 |
| 31 | 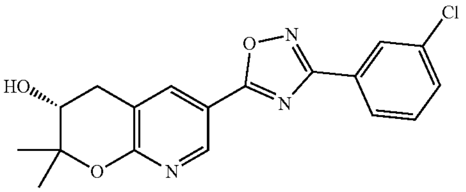 [SMILES: CC1(C)Oc2ncc(-c3nc(-c4cccc(Cl)c4)no3)cc2C[C@H]1O] | 152 | 212 |
| 32 | 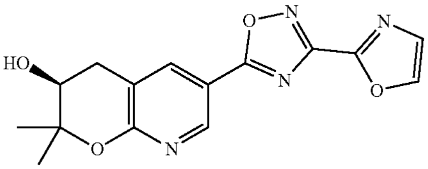 [SMILES: CC1(C)Oc2ncc(-c3nc(-c4ncco4)no3)cc2C[C@@H]1O] | 65 | 213 |
| 33 | 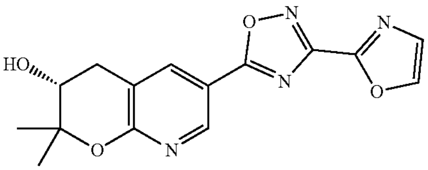 [SMILES: CC1(C)Oc2ncc(-c3nc(-c4ncco4)no3)cc2C[C@H]1O] | 76 | 214 |

TABLE 1-continued
| Example # | Structure | Luciferase IC50 nM | ID NUMBER SMS21032-0 |
|---|---|---|---|
| 34 | 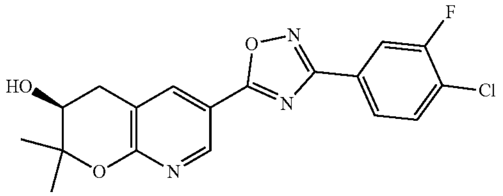 [SMILES: CC1(C)Oc2ncc(-c3nc(-c4ccc(Cl)c(F)c4)no3)cc2C[C@@H]1O] | 39 | 215 |
| 35 | 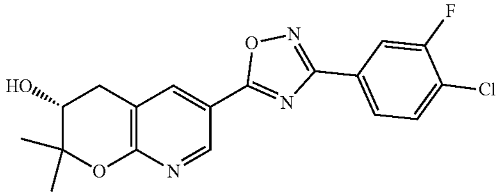 [SMILES: CC1(C)Oc2ncc(-c3nc(-c4ccc(Cl)c(F)c4)no3)cc2C[C@H]1O] | 22 | 216 |
| 36 | 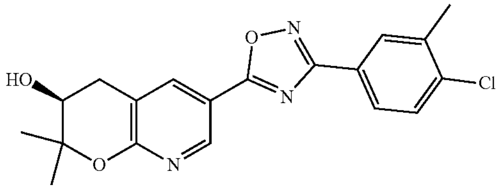 [SMILES: Cc1cc(-c2noc(-c3cnc4c(c3)C[C@H](O)C(C)(C)O4)n2)ccc1Cl] | 52 | 217 |
| 37 | 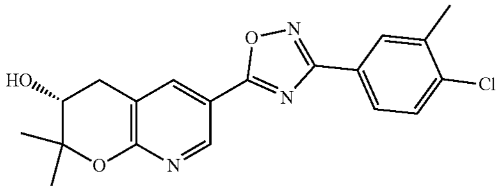 [SMILES: Cc1cc(-c2noc(-c3cnc4c(c3)C[C@@H](O)C(C)(C)O4)n2)ccc1Cl] | 50 | 218 |
| 38 | 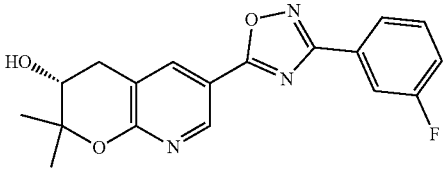 [SMILES: CC1(C)Oc2ncc(-c3nc(-c4cccc(F)c4)no3)cc2C[C@H]1O] | 148 | 259 |
| 39 | 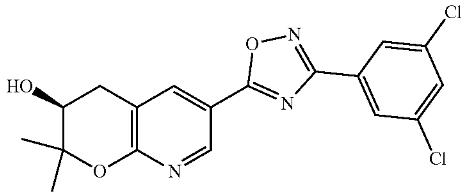 [SMILES: CC1(C)Oc2ncc(-c3nc(-c4cc(Cl)cc(Cl)c4)no3)cc2C[C@@H]1O] | 1253 | 260 |
| 40 | 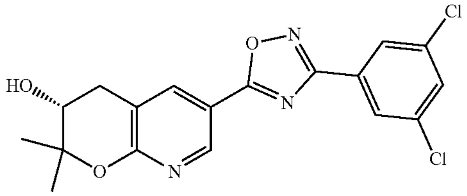 [SMILES: CC1(C)Oc2ncc(-c3nc(-c4cc(Cl)cc(Cl)c4)no3)cc2C[C@H]1O] | 843 | 261 |

Representative Syntheses Follow:

Experimental Section

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. $^1H$ chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm×4.6 mm×3.5 um), Flow Rate: 2.0 ml/min, the column temperature: 40° C.

Example 1: The synthesis of ethyl 2,2-dimethyl-2H-pyrano[2,3-b]pyridine-6-carboxylate (0097-1)

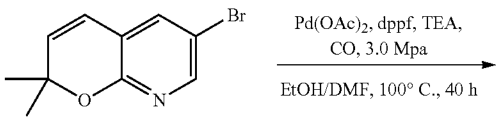

0095-3

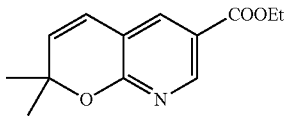

0097-1

A solution of 0095-3 (2 g, 8.4 mmol), $Pd(OAc)_2$ (190 mg, 0.84 mmol), dppf (932 mg, 1.68 mmol), TEA (3.4 g, 33.6 mmol) in EtOH/DMF (1/1 v/v, 20 mL) was stirred at 100° C. for 40 h under CO atmosphere (3 Mpa). After the consumption of starting material (by LCMS), the solution was concentrated in vacuo, purified by column (PE:EA=15:1) to give the product 0097-1 (1 g, 51% yield) as a white solid.

The synthesis of ethyl 4-bromo-3-hydroxy-2,2-dimethyl-3,4-dihydro-2H-pyrano[2,3-b]pyridine-6-carboxylate (0097-2).

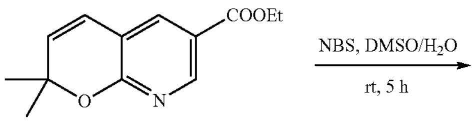

0097-1

-continued

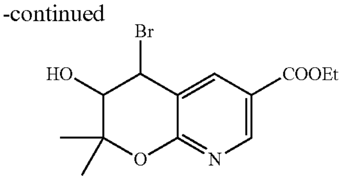

0097-2

To a stirred solution of compound 0097-1 (700 mg, 3 mmol) in DMSO/$H_2O$ (10 ml) was added NBS (1.6 g, 9 mmol). The mixture was stirred at room temperature for 5 h. After the consumption of starting material (by LCMS), the reaction solution was extracted with ethyl acetate, the combined organic phases were dried over anhydrous sodium sulfate, filtered, concentrated in vacuo, purified by column (PE:EA=3:1) to afford the 0097-2 (750 mg, 76% yield) as a white solid.

The synthesis of ethyl 2,2-dimethyl-2,7b-dihydro-1aH-oxireno[2',3':4,5]pyrano[2,3-b]pyridine-6-carboxylate (0097-3).

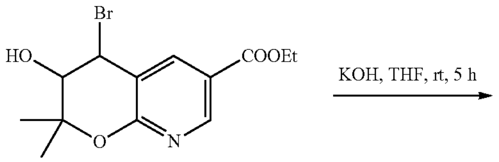

0097-2

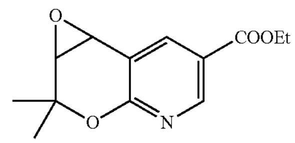

0097-3

A solution of 0097-2 (750 mg, 2.28 mmol) and KOH (255 mg, 4.56 mmol) in THF (10 mL) was stirred at room temperature for 5 h. After the consumption of starting material (by LCMS), the solution was concentrated in vacuo, purified by column (PE:EA=3:1) to give the product 0097-3 (500 mg, 88% yield) as a white solid.

The synthesis of ethyl 3-hydroxy-2,2-dimethyl-3,4-dihydro-2H-pyrano[2,3-b]pyridine-6-carboxylate (0097-4).

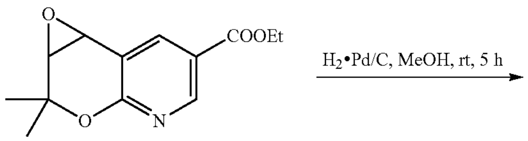

0097-3

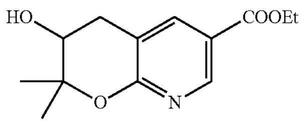

0097-4

To a stirred solution of compound 0097-3 (300 mg, 1.2 mmol) in MeOH (10 mL) was added Pd/C (30 mg, 10% w/w). The mixture was stirred at room temperature for 5 h under $H_2$ atmosphere (1.0 atm). After the consumption of starting material (by LCMS), the reaction mixture was filtered, washed with MeOH, and the filtrate was concentrated in vacuo, purified by column (PE:EA=2:1) to give the product 0097-4 (280 mg, 93% yield) as a colorless oil. The synthesis of 3-hydroxy-2,2-dimethyl-3,4-dihydro-2H-pyrano[2,3-b]pyridine-6-carboxylic acid (0097-5).

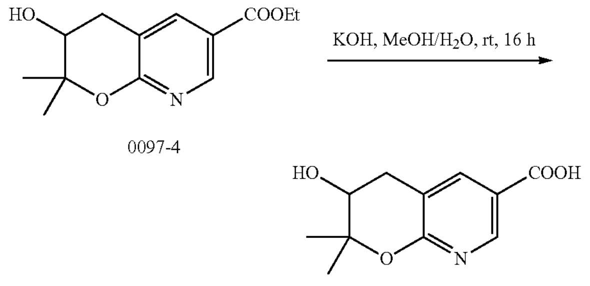

0097-4

0097-5

The mixture of 0097-4 (280 mg, 1.12 mmol) and KOH (314 mg, 5.6 mmol) in $MeOH/H_2O$ (4/1, 10 mL) was stirred at room temperature overnight. Then the reaction mixture was neutralized with 1 M HCl till pH reached to 6.0. The resulting mixture was concentrated in vacuo, purified by prep-HPLC to give the product 0097-5 (200 mg, 80% yield) as a white solid.

The synthesis of 6-(3-(4-bromophenyl)-1,2,4-oxadiazol-5-yl)-2,2-dimethyl-3,4-dihydro-2H-pyrano[2,3-b]pyridin-3-ol (SMS21032-0097-01).

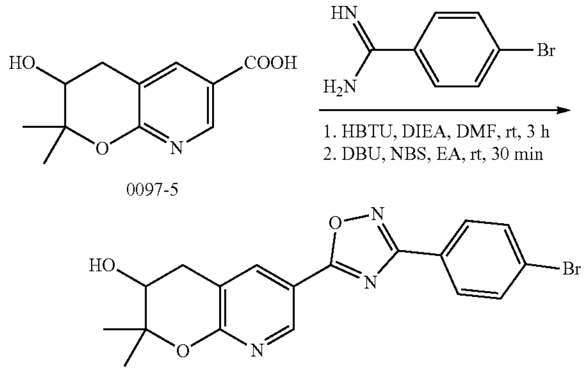

0097-5

SMS21032-0097-01

To a stirred solution of compound 0097-5 (150 mg, 0.67 mmol), 4-bromo-N'-hydroxybenzimidamide (160 mg, 0.81 mmol) and HBTU (384 mg, 1.01 mmol) in DMF (5 ml) was added DIEA (173 mg, 1.34 mmol). The mixture was stirred at room temperature for 3 h. After the consumption of starting material (by LCMS), the reaction solution was extracted with ethyl acetate, the combined organic phases were dried over anhydrous sodium sulfate, filtered, concentrated in vacuo. To the crude in ethyl acetate (5 mL) was added DBU (204 mg, 1.34 mmol) and NBS (240 mg, 1.34 mmol). The mixture solution was stirred at room temperature for 30 min. After the consumption of starting material (by LCMS), the reaction mixture was concentrated in vacuo, purified by prep-HPLC to give the desired product SMS21032-0097-01 (30 mg, 11% yield) as a white solid Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 100%, Rt=2.197 min; MS Calcd.: 402.24; MS Found: 402.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.59%, Rt=10.582 min.

$^1H$ NMR (400 MHz, $CDCl_3$) δ 8.94 (s, 1H), 8.23 (s, 1H), 8.01 (d, J=8.4 Hz, 2H), 7.64 (d, J=8.8 Hz, 2H), 3.97 (t, J=5.2 Hz, 1H), 3.17-3.23 (m, 1H), 2.94-2.99 (m, 1H), 1.51 (s, 3H), 1.46 (s, 3H).

Example 2: The synthesis of ethyl 4-amino-3-hydroxy-2,2-dimethyl-3,4-dihydro-2H-pyrano[2,3-b]pyridine-6-carboxylate (0098-2)

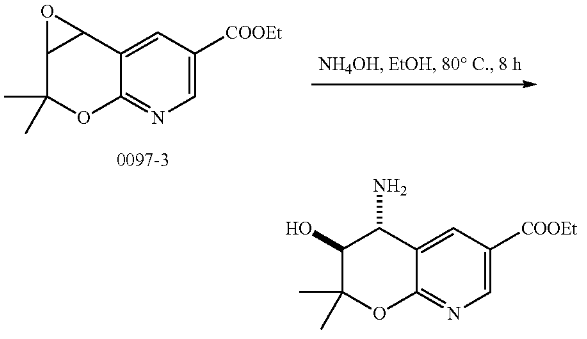

0097-3 racemic
0098-2

To a stirred solution of compound 0097-3 (330 mg, 1.33 mmol) in EtOH (10 ml) was added $NH_4OH$ (12 mL). The mixture was stirred at 80° C. for 8 h. After the consumption of starting material (by LCMS), the reaction solution was concentrated in vacuo to give the crude product 0098-2 (350 mg, 98.9% yield) as a yellow solid.

The synthesis of ethyl 4-(tert-butoxycarbonylamino)-3-hydroxy-2,2-dimethyl-3,4-dihydro-2H-pyrano[2,3-b]pyridine-6-carboxylate (0098-3).

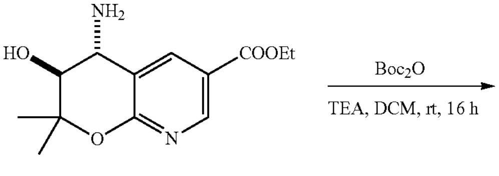

racemic
0098-2

-continued

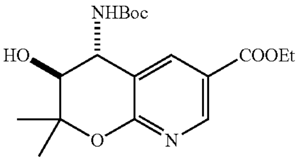

racemic
0098-3

-continued

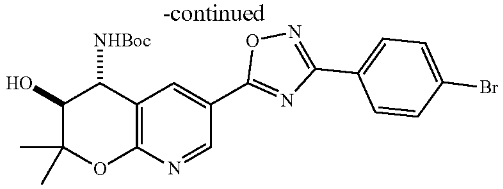

racemic
0098-5

To a stirred solution of compound 0098-2 (350 mg, 1.32 mmol) and TEA (267 mg, 2.64 mmol) in DCM (10 ml) was added $Boc_2O$ (432 mg, 1.98 mmol). The mixture was stirred at room temperature overnight. After the consumption of starting material (by LCMS), the reaction solution was concentrated in vacuo, purified by column (PE:EA=3:1) to give the product 0098-3 (170 mg, 35.2% yield) as colorless oil.

The synthesis of 4-(tert-butoxycarbonylamino)-3-hydroxy-2,2-dimethyl-3,4-dihydro-2H-pyrano[2,3-b]pyridine-6-carboxylic acid (0098-4).

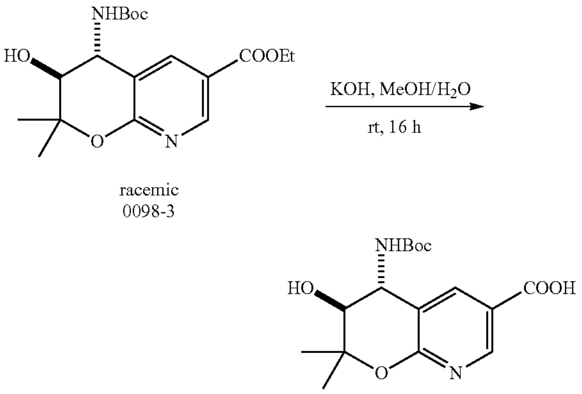

racemic
0098-3 racemic
0098-4

A solution of 0098-3 (170 mg, 0.46 mmol) and KOH (130 mg, 2.3 mmol) in $MeOH/H_2O$ (4/1, 5 mL) was stirred at room temperature overnight. After the consumption of starting material (by LCMS), the reaction mixture was neutralized with 1 M HCl till pH reached 6. The solution was concentrated in vacuo, purified by prep-HPLC to give the product 0098-4 (120 mg, 77% yield) as a white solid.

The synthesis of tert-butyl-6-(3-(4-bromophenyl)-1,2,4-oxadiazol-5-yl)-3-hydroxy-2,2-dimethyl-3,4-dihydro-2H-pyrano[2,3-b]pyridin-4-ylcarbamate (0098-5).

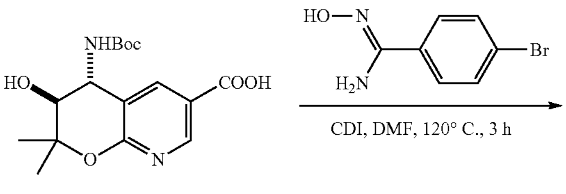

racemic
0098-4

To a stirred solution of compound 0098-4 (120 mg, 0.36 mmol) in DMF (10 ml) was added CDI (121 mg, 0.72 mmol). Stirred for 30 min at room temperature, then 4-bromo-N'-hydroxybenzimidamide (154 mg, 0.72 mmol) was added. The mixture was stirred for 3 h at 120° C. After the consumption of starting material (by LCMS), the reaction mixture was concentrated in vacuo, purified by column (DCM:MeOH=50:1) to give the product 0098-5 (150 mg, 80.6% yield) as a white solid.

The synthesis of 4-amino-6-(3-(4-bromophenyl)-1,2,4-oxadiazol-5-yl)-2,2-dimethyl-3,4-dihydro-2H-pyrano[2,3-b]pyridin-3-ol (SMS21032-0098-01).

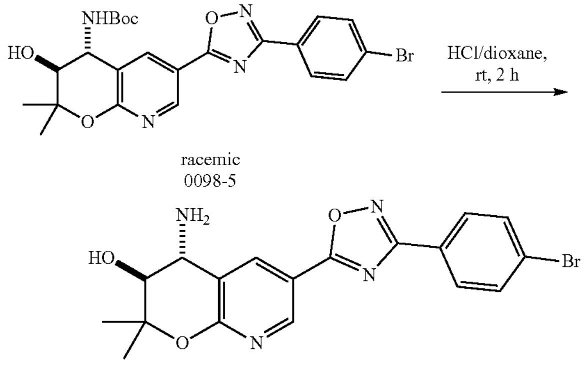

racemic
0098-5 racemic
SMS21032-0098-01

A solution of compound 0098-5 (100 mg, 0.2 mmol) in HCl/dioxane (4 M, 5 ml) was stirred at room temperature for 2 h. After the consumption of starting material (by LCMS), the reaction solution was concentrated in vacuo, purified by prep-HPLC to give the desired product SMS21032-0098-01 (21 mg, 25.3% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 96.20%, Rt=2.061 min; MS Calcd.: 417.26; MS Found: 417.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 98.49%, Rt=9.810 min.

$^1$H NMR (400 MHz, $CDCl_3$) δ 8.98 (d, J=2.0 Hz, 1H), 8.55-8.56 (m, 1H), 8.02-8.04 (m, 2H), 7.64-7.66 (m, 2H), 3.79 (d, J=10 Hz, 1H), 3.43 (d, J=10 Hz, 1H), 3.02 (br., 1H), 1.64 (s, 3H), 1.35 (s, 3H)

Examples 3 and 4: The synthesis of ethyl (S)-6-(3-(4-bromophenyl)-1,2,4-oxadiazol-5-yl)-2-methyl-3,4-dihydro-2H-pyrano[2,3-b]pyridine (SMS21032-0130) and ethyl (R)-6-(3-(4-bromophenyl)-1,2,4-oxadiazol-5-yl)-2-methyl-3,4-dihydro-2H-pyrano[2,3-b]pyridine (SMS21032-0131)

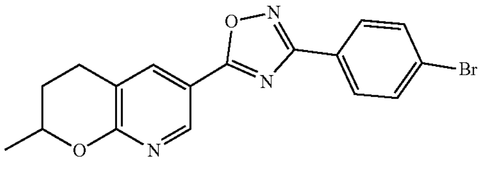

SMS21032-0084

SFC resolution

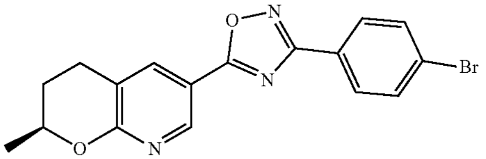

SMS21032-0130

+

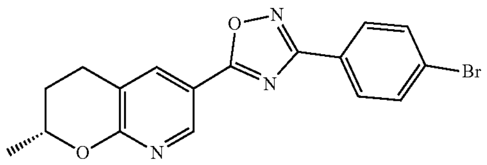

SMS21032-0131

SMS21032-0130:

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min. Purity is 99.3%. Rt=2.496 min; MS Calcd.: 371.0; MS Found: 371.8 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is 98.0%. Rt=11.975 min.

$^1$HNMR (400 MHz, $CDCl_3$) δ 8.93 (d, J=2.0 Hz, 1H), 8.18 (d, J=2.0 Hz, 1H), 8.04 (d, J=8.8 Hz, 2H), 7.66 (d, J=8.8 Hz, 2H), 4.53-4.44 (m, 1H), 3.03-2.88 (m, 2H), 2.17-2.09 (m, 1H), 1.87-1.75 (m, 1H), 1.54 (d, J=6.4 Hz, 3H).

SMS21032-0131:

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min. Purity is 99.4%. Rt=2.491 min; MS Calcd.: 371.0; MS Found: 372.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is 97.0%. Rt=11.972 min.

$^1$HNMR (400 MHz, $CDCl_3$) δ 8.93 (d, J=2.0 Hz, 1H), 8.17 (d, J=2.0 Hz, 1H), 8.03 (d, J=8.4 Hz, 2H), 7.65 (d, J=8.4 Hz, 2H), 4.52-4.43 (m, 1H), 3.02-2.87 (m, 2H), 2.16-2.08 (m, 1H), 1.87-1.75 (m, 1H), 1.53 (d, J=6.0 Hz, 3H).

Example 5: The synthesis of 6-(3-(4-bromophenyl)-1,2,4-oxadiazol-5-yl)-2,2-dimethyl-3,4-dihydro-2H-pyrano[2,3-b]pyridin-4-ol (SMS21032-0143)

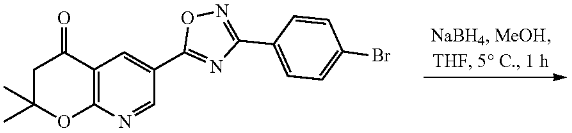

SMS21032-0142

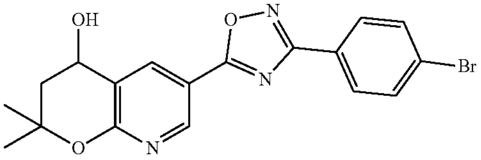

SMS21032-0143

To the solution of SMS21032-0142 (40 mg, 0.1 mmol) in MeOH (1 mL)/THF (2 mL) was added $NaBH_4$ (4 mg, 0.1 mmol) at 5° C., then the mixture was stirred at 5° C. for 1 h. Concentrated to oil, which was purified by Prep-HPLC to give SMS21032-0143 (8 mg, yield: 20%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0%

[water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity 100%, Rt=2.245 min; MS Calcd.: 401.0; MS Found: 402.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity 99.3%, Rt=10.808 min; MS Calcd.: 401.0; MS Found: 402.2 $[M+H]^+$.

$^1H$ NMR (400 MHz, $CDCl_3$) δ 9.01 (d, J=2.4 Hz, 1H), 8.63 (d, J=1.6 Hz, 1H), 8.04 (d, J=8.4 Hz, 2H), 7.66 (d, J=8.8 Hz, 2H), 4.98-5.06 (m, 1H), 2.33 (dd, J=13.6, 6.0 Hz, 1H), 2.10 (d, J=7.6 Hz, 1H), 1.96 (dd, J=13.4, 10.2 Hz, 1H), 1.60 (s, 3H), 1.44 (s, 3H).

Example 6: The synthesis of (R)-3-hydroxy-2,2-dimethyl-3,4-dihydro-2H-pyrano[2,3-b]pyridine-6-carboxylic acid (0097-5a)

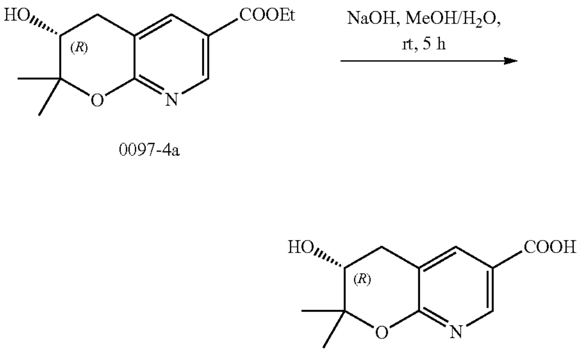

0097-4a 0097-5a

A solution of 0097-4a (180 mg, 0.72 mmol) and NaOH (144 mg, 3.6 mmol) in MeOH/$H_2O$ (4/1, 10 mL) was stirred at room temperature for 5 h. After the consumption of starting material (by LCMS), the reaction mixture was neutralized with 1 M HCl till pH reached 6. The solution was concentrated in vacuo, purified by prep-HPLC to give the product 0097-5a (130 mg, 81% yield) as a white solid.

The synthesis of (R)-6-(3-(4-bromophenyl)-1,2,4-oxadiazol-5-yl)-2,2-dimethyl-3,4-dihydro-2H-pyrano[2,3-b]pyridin-3-ol (SMS21032-0151-01).

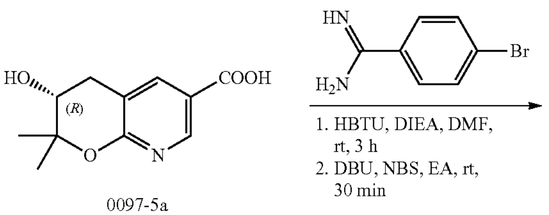

0097-5a

-continued

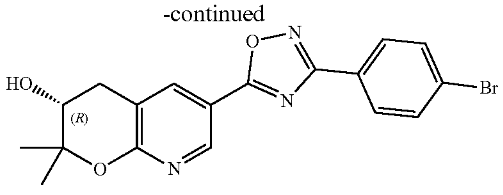

absolute stereochemistry
SMS21032-0151-01

To a stirred solution of compound 0097-5a (70 mg, 0.32 mmol), 4-bromobenzimidamide (77 mg, 0.39 mmol) and HBTU (183 mg, 0.48 mmol) in DMF (5 ml) was added DIEA (83 mg, 0.64 mmol). The mixture was stirred at room temperature for 3 h. After the consumption of starting material (by LCMS), the reaction solution was extracted with ethyl acetate, the combined organic phases were dried over anhydrous sodium sulfate, filtered, concentrated in vacuo. To the crude in ethyl acetate (5 mL) was added DBU (98 mg, 0.64 mmol) and NBS (114 mg, 0.64 mmol). The mixture solution was stirred at room temperature for 30 min. After the consumption of starting material (by LCMS), the reaction mixture was concentrated in vacuo, purified by prep-HPLC to give the desired product SMS21032-0151-01 (27 mg, 21% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 96.88%, Rt=2.212 min; MS Calcd.: 402.24; MS Found: 401.8 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 96.03%, Rt=10.749 min.

$^1H$ NMR (400 MHz, $CDCl_3$) δ 8.94 (d, J=2.0 Hz, 1H), 8.26 (d, J=1.2 Hz, 1H), 7.99 (d, J=8.4 Hz, 2H), 7.63 (d, J=8.4 Hz, 2H), 3.98 (t, J=4.8 Hz, 1H), 3.17-3.23 (m, 1H), 2.97-3.03 (m, 1H), 1.52 (s, 3H), 1.46 (s, 3H).

Example 7: The synthesis of (S)-3-hydroxy-2,2-dimethyl-3,4-dihydro-2H-pyrano[2,3-b]pyridine-6-carboxylic acid (0097-5b)

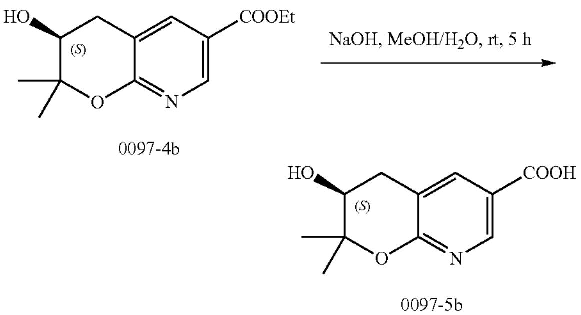

0097-4b 0097-5b

A solution of 0097-4b (190 mg, 0.76 mmol) and NaOH (152 mg, 3.8 mmol) in MeOH/$H_2O$ (4/1, 10 mL) was stirred at room temperature overnight. After the consumption of starting material (by LCMS), the reaction mixture was neutralized with 1 M HCl till pH reached 6. The solution was concentrated in vacuo, purified by prep-HPLC to give the product 0097-5b (140 mg, 82.3% yield) as a white solid.

The synthesis of (S)-6-(3-(4-bromophenyl)-1,2,4-oxadiazol-5-yl)-2,2-dimethyl-3,4-dihydro-2H-pyrano[2,3-b]pyridin-3-ol (SMS21032-0152-01).

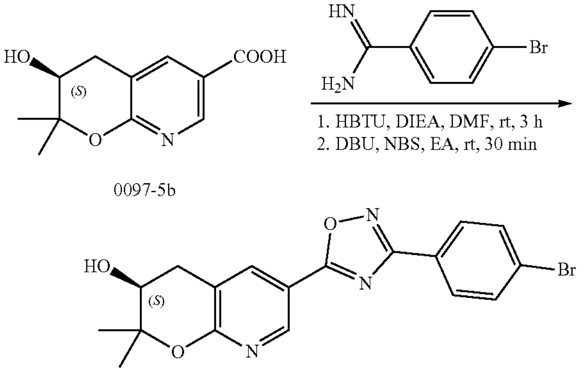

0097-5b absolute stereochemistry
SMS21032-0152-01

To a stirred solution of compound 0097-5b (70 mg, 0.32 mmol), 4-bromobenzimidamide (77 mg, 0.39 mmol) and HBTU (183 mg, 0.48 mmol) in DMF (5 ml) was added DIEA (83 mg, 0.64 mmol). The mixture was stirred at room temperature for 3 h. After the consumption of starting material (by LCMS), the reaction solution was extracted with ethyl acetate, the combined organic phases were dried over anhydrous sodium sulfate, filtered, concentrated in vacuo. To the crude in ethyl acetate (5 mL) was added DBU (98 mg, 0.64 mmol) and NBS (114 mg, 0.64 mmol). The mixture solution was stirred at room temperature for 30 min. After the consumption of starting material (by LCMS), the reaction mixture was concentrated in vacuo, purified by prep-HPLC to give the desired product SMS21032-0152-01 (25 mg, 19.5% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 100%, Rt=2.214 min; MS Calcd.: 402.24; MS Found: 401.8 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.30%, Rt=10.750 min.

$^1H$ NMR (400 MHz, $CDCl_3$) δ 8.93 (d, J=1.6 Hz, 1H), 8.24 (d, J=0.8 Hz, 1H), 8.00 (d, J=8.4 Hz, 2H), 7.63 (d, J=8.4 Hz, 2H), 3.97 (t, J=4.8 Hz, 1H), 3.17-3.23 (m, 1H), 2.96-3.02 (m, 1H), 1.51 (s, 3H), 1.45 (s, 3H).

Example 8: The synthesis of (3R,4S)-ethyl 3,4-dihydroxy-2,2-dimethyl-3,4-dihydro-2H-pyrano[2,3-b]pyridine-6-carboxylate (0164-2)

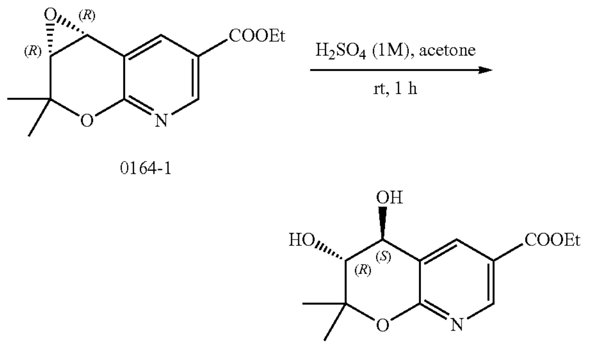

0164-1

0164-2

To a stirred solution of compound 0164-1 (120 mg, 0.48 mmol) in acetone was added $H_2SO_4$ (1 M, 3 mL). The mixture was stirred for 1 h at room temperature. The reaction mixture was neutralized to pH=7 using $NaHCO_3$. Dichloromethane was added to the reaction mixture, and the organic phase separated. The aqueous layer was extracted with dichloromethane, and the organic layers were combined and dried over $Na_2SO_4$. The solvents were removed under reduced pressure, and the residue was purified by column (PE/EA=2:1) to give the product 0164-2 (80 mg, 62.5% yield) as yellow oil.

The synthesis of (3R,4S)-3,4-dihydroxy-2,2-dimethyl-3,4-dihydro-2H-pyrano[2,3-b]pyridine-6-carboxylic acid (0164-3).

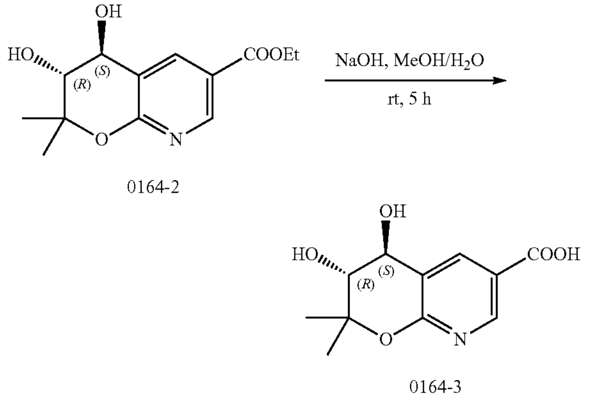

0164-2

0164-3

A solution of 0164-2 (80 mg, 0.3 mmol) and NaOH (60 mg, 1.5 mmol) in MeOH/$H_2O$ (4/1, 5 mL) was stirred at room temperature for 5 h. After the consumption of starting material (by LCMS), the reaction mixture was neutralized with 1 M HCl till pH reached 6. The solution was concentrated in vacuo, purified by prep-HPLC to give the product 0164-3 (55 mg, 76.7% yield) as a white solid.

The synthesis of (3R,4S)-6-(3-(4-bromophenyl)-1,2,4-oxadiazol-5-yl)-2,2-dimethyl-3,4-dihydro-2H-pyrano[2,3-b]pyridine-3,4-diol (SMS21032-0164-01).

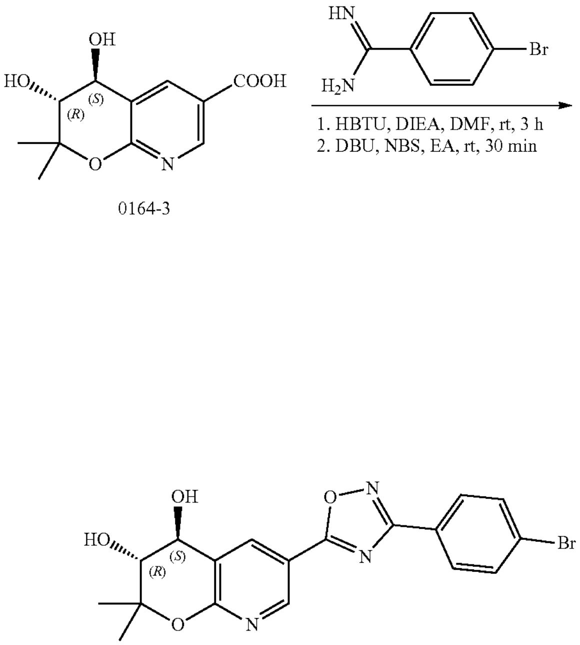

0164-3 absolute stereochemistry
SMS21032-0164-01

To a stirred solution of compound 0164-3 (55 mg, 0.23 mmol), 4-bromobenzimidamide (56 mg, 0.28 mmol) and HBTU (133 mg, 0.35 mmol) in DMF (5 ml) was added DIEA (60 mg, 0.46 mmol). The mixture was stirred at room temperature for 3 h. After the consumption of starting material (by LCMS), the reaction solution was extracted with ethyl acetate, the combined organic phases were dried over anhydrous sodium sulfate, filtered, concentrated in vacuo. To the crude in ethyl acetate (5 mL) was added DBU (70 mg, 0.46 mmol) and NBS (82 mg, 0.34 mmol). The mixture solution was stirred at room temperature for 30 min. After the consumption of starting material (by LCMS), the reaction mixture was concentrated in vacuo, purified by prep-HPLC to give the desired product SMS21032-0164-01 (28 mg, 29.2% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 96.88%, Rt=2.078 min; MS Calcd.: 418.24; MS Found: 418.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.50%, Rt=9.860 min.

$^1H$ NMR (400 MHz, $CDCl_3$) δ 9.03 (d, J=2.0 Hz, 1H), 8.65 (s, 1H), 8.04 (d, J=8.4 Hz, 2H), 7.66 (d, J=8.0 Hz, 2H), 4.76 (d, J=9.2 Hz, 1H), 3.73 (d, J=9.2 Hz, 1H), 1.64 (s, 3H), 1.38 (s, 3H).

Example 9: The synthesis of (3S,4R)-ethyl 3,4-dihydroxy-2,2-dimethyl-3,4-dihydro-2H-pyrano[2,3-b]pyridine-6-carboxylate (0165-2)

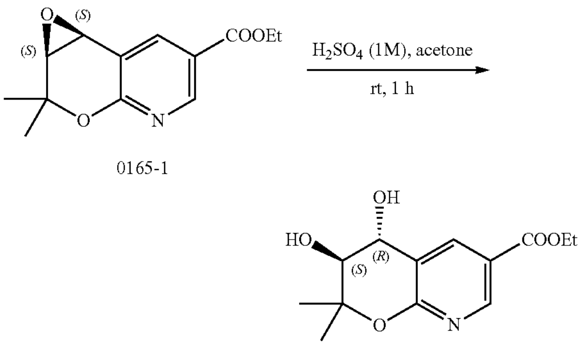

0165-1

0165-2

To a stirred solution of compound 0165-1 (130 mg, 0.52 mmol) in acetone was added $H_2SO_4$ (1M, 3 mL). The mixture was stirred for 1 h at room temperature. The reaction mixture was neutralized to pH=7 using $NaHCO_3$. Dichloromethane was added to the reaction mixture, and the organic phase separated. The aqueous layer was extracted with dichloromethane, and the organic layers were combined and dried over $Na_2SO_4$. The solvents were removed under reduced pressure, and the residue was purified by column (PE:EA=2:1) to give the product 0165-2 (90 mg, 64.7% yield) as a yellow oil.

The synthesis of (3S,4R)-3,4-dihydroxy-2,2-dimethyl-3,4-dihydro-2H-pyrano[2,3-b]pyridine-6-carboxylic acid (0165-3).

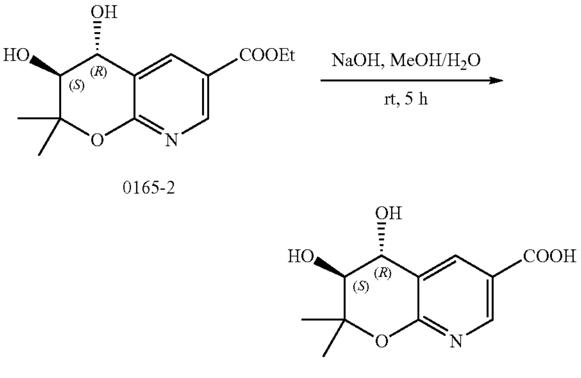

0165-2

0165-3

A solution of 0165-2 (90 mg, 0.34 mmol) and NaOH (68 mg, 1.7 mmol) in MeOH/$H_2O$ (4/1, 5 mL) was stirred at room temperature for 5 h. After the consumption of starting material (by LCMS), the reaction mixture was neutralized with 1 M HCl till pH reached 6. The solution was concentrated in vacuo, purified by prep-HPLC to give the product 0165-3 (60 mg, 73.8% yield) as a white solid.

The synthesis of (3S,4R)-6-(3-(4-bromophenyl)-1,2,4-oxadiazol-5-yl)-2,2-dimethyl-3,4-dihydro-2H-pyrano[2,3-b]pyridine-3,4-diol (SMS21032-0165-01).

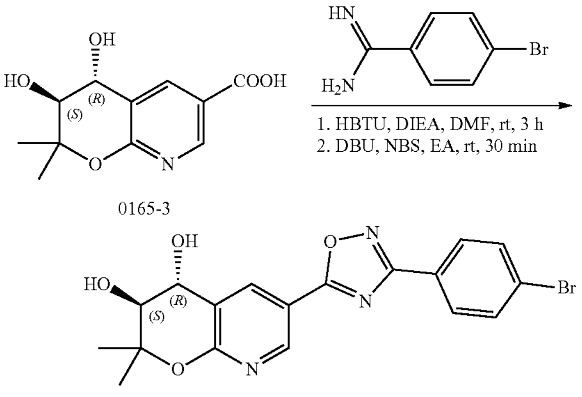

0165-3 absolute stereochemistry
SMS21032-0165-01

To a stirred solution of compound 0165-3 (60 mg, 0.25 mmol), 4-bromobenzimidamide (60 mg, 0.3 mmol) and HBTU (143 mg, 0.38 mmol) in DMF (5 ml) was added DIEA (65 mg, 0.5 mmol). The mixture was stirred at room temperature for 3 h. After the consumption of starting material (by LCMS), the reaction solution was extracted with ethyl acetate, the combined organic phases were dried over anhydrous sodium sulfate, filtered, concentrated in vacuo. To the crude in ethyl acetate (5 mL) was added DBU (76 mg, 0.5 mmol) and NBS (89 mg, 0.5 mmol). The mixture solution was stirred at room temperature for 30 min. After the consumption of starting material (by LCMS), the reaction mixture was concentrated in vacuo, purified by prep-HPLC to give the desired product SMS21032-0165-01 (27 mg, 26% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 97.44%, Rt=2.076 min; MS Calcd.: 418.24; MS Found: 418.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=9.858 min.

$^1H$ NMR (400 MHz, $CDCl_3$) δ 9.03 (d, J=2.0 Hz, 1H), 8.63 (d, J=1.2 Hz, 1H), 8.04 (d, J=8.4 Hz, 2H), 7.66 (d, J=8.8 Hz, 2H), 4.75 (d, J=9.2 Hz, 1H), 3.73 (d, J=8.8 Hz, 1H), 1.64 (s, 3H), 1.38 (s, 3H).

Example 10 and 11: The synthesis of (R)-6-(3-(4-bromophenyl)-1,2,4-oxadiazol-5-yl)-2,2-dimethyl-3,4-dihydro-2H-pyrano[2,3-b]pyridin-4-ol (SMS21032-0171) and (S)-6-(3-(4-bromophenyl)-1,2,4-oxadiazol-5-yl)-2,2-dimethyl-3,4-dihydro-2H-pyrano[2,3-b]pyridin-4-ol (SMS21032-0172)

The synthesis of 6-(3-(4-bromophenyl)-1,2,4-oxadiazol-5-yl)-2,2-dimethyl-2H-pyrano[2,3-b]pyridin-4(3H)-one (SMS21032-0142) The synthesis of 1-(5-bromo-2-methoxypyridin-3-yl)-3-methylbut-2-en-1-one (142-1)

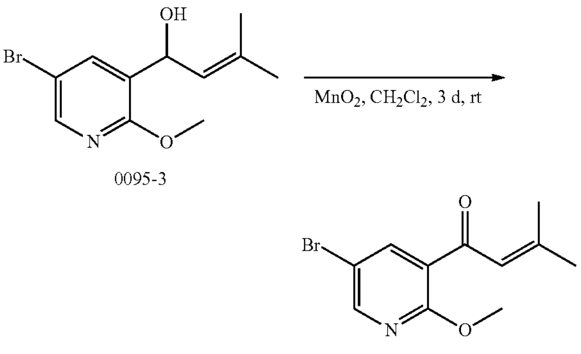

0095-3

142-1

To a solution of 0095-3 (1 g, 3.67 mmol) in DCM (160 mL) was added $MnO_2$ (6.71 g, 77.17 mmol) at room temperature, then the mixture was stirred at room temperature for 3 days. Filtration and concentrated to oil, which was purified by c.c. (EA:PE=1:30) to give 142-1 (0.71 g, yield: 72%) as yellow liquid.

The synthesis of 6-bromo-2,2-dimethyl-2H-pyrano[2,3-b]pyridin-4(3H)-one (142-2)

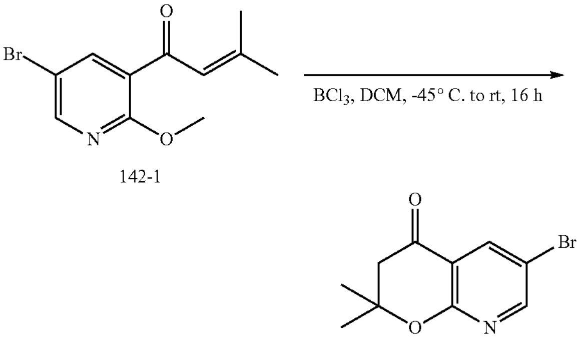

142-1

142-2

To the solution of 142-1 (2.9 g, 10.74 mmol) in DCM (150 mL) was added $BCl_3$ (55 mL) at −45° C. dropwise, when addition was complete, the mixture was stirred at room temperature for 16 h. Then the reaction was quenched with sat $NaHCO_3$, diluted with DCM (20 mL), washed with brine (50 ml), dried in $Na_2SO_4$. Filtration and concentrated to oil, which was purified by c.c. (EA:PE=1:3) to give 142-2 (1.3 g, yield: 47%) as a yellow solid.

The synthesis of 6'-bromo-2',2'-dimethyl-2',3'-dihydrospiro[[1,3]dioxolane-2,4'-pyrano[2,3-b]pyridine](142-3)

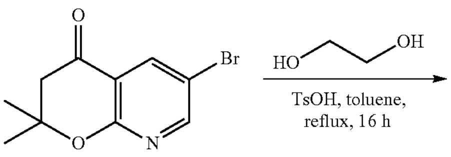

142-2

-continued

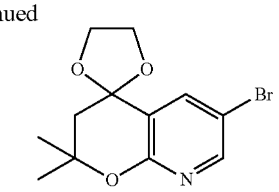

142-3

To the solution of 142-2 (200 mg, 0.78 mmol) in toluene (10 mL) was added ethylene glycol (97 mg, 1.56 mmol), TsOH (8 mg, 0.16 mmol), then the mixture was refluxed for 16 h. The mixture was washed with sat $NaHCO_3$ (20 ml), dried in $Na_2SO_4$. Filtration and concentrated to solid to give 142-3 (100 mg, yield: 43%) as a yellow solid.

The synthesis of methyl 2',2'-dimethyl-2',3'-dihydrospiro[[1,3]dioxolane-2,4'-pyrano[2,3-b]pyridine]-6'-carboxylate (142-4)

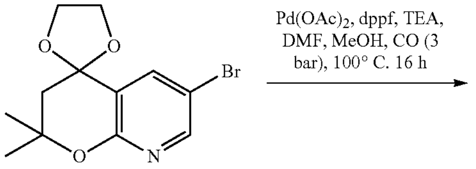

142-3

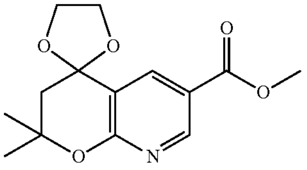

142-4

To the solution of 142-3 (400 mg, 1.33 mmol) in DMF (6 mL)/MeOH (6 mL) was added TEA (674 mg, 6.66 mmol,), dppf (111 mg, 0.20 mmol), $Pd(OAc)_2$ (45 mg, 0.20 mmol), then the mixture was heated to 100° C. for 16 h in CO (3 bar). Filtration and concentrated the filtrate, the residue was diluted with EA (50 mL), washed with brine (30 mL), dried in $Na_2SO_4$. Filtration and concentrated the filtrate to oil, which was purified by c.c. (EA:PE=1:4) to give 142-4 (330 mg, yield: 89%) as yellow oil.

The synthesis of 2',2'-dimethyl-2',3'-dihydrospiro[[1,3]dioxolane-2,4'-pyrano[2,3-b]pyridine]-6'-carboxylic acid (142-5)

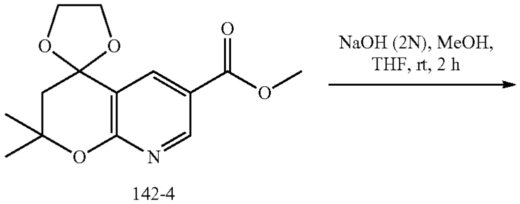

142-4

-continued

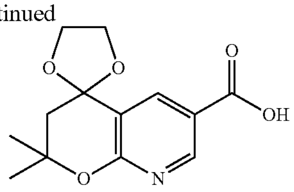

142-5

To the solution of 142-4 (110 mg, 0.4 mmol) in MeOH (2 mL)/THF (1 mL) was added the solution of NaOH (40 mg, 0.99 mmol) in $H_2O$ (0.5 mL), then the mixture was stirred at room temperature for 2 h. Concentrated to solid, acidified with HCl (2N) to pH=5, then concentrated to give 142-5 as a crude solid.

The synthesis of 6'-(3-(4-bromophenyl)-1,2,4-oxadiazol-5-yl)-2',2'-dimethyl-2',3'-dihydrospiro[[1,3]dioxolane-2,4'-pyrano[2,3-b]pyridine](SMS21032-0169)

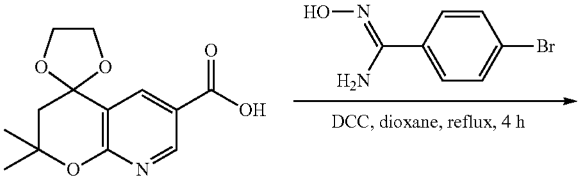

142-5

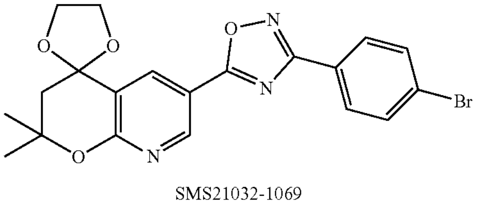

SMS21032-1069

To the solution of 142-5 (crude), 4-bromo-N'-hydroxybenzamidine (105 mg, 0.50 mmol) in dioxane (15 mL) was added DCC (131 mg, 0.64 mmol) at room temperature, then the mixture was refluxed for 4 h. Concentrated to oil, the residue was further purified by prep-HPLC to give SMS21032-0169 (10 mg, 5.6% yield for two steps) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 96.6%, Rt=2.481 min; MS Calcd: 399.0; MS Found: 400.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 97.0%, Rt=11.932 min. MS Calcd: 399.0; MS Found: 400.2 $[M+H]^+$.

$^1H$ NMR (400 MHz, $CDCl_3$) δ 9.07 (d, J=2.4 Hz, 1H), 8.50 (d, J=2.4 Hz, 1H), 8.03-8.07 (m, 2H), 7.63-7.68 (m, 2H), 4.30-4.36 (m, 2H), 4.12-4.20 (m, 2H), 2.23 (s, 2H), 1.56 (s, 6H).

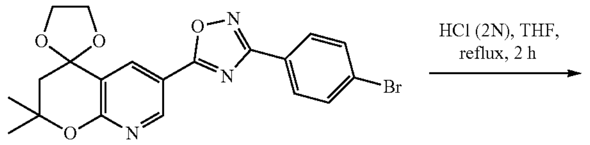

SMS21032-1069

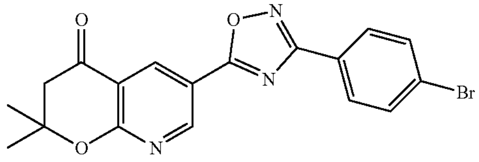

SMS21032-1042

To the solution of SMS21032-0169 (crude) in THF (3 mL) was added HCl (2 N, 0.2 mL), then the mixture was refluxed for 2 h. Concentrated to oil, diluted with DCM (10 mL), washed with sat $NaHCO_3$, dried over $Na_2SO_4$. Filtration and concentrated the filtrate to solid.

The crude was washed with MeOH to give SMS21032-0142 (25 mg, yield: 16%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 96.6%, Rt=2.481 min; MS Calcd: 399.0; MS Found: 400.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is 96.4%. Rt=7.558 min. Purity: 97.0%, Rt=11.932 min. MS Calcd: 399.0; MS Found: 400.2 $[M+H]^+$.

$^1H$ NMR (400 MHz, $CDCl_3$) δ 9.28 (d, J=2.4 Hz, 1H), 8.96 (d, J=2.4 Hz, 1H), 8.04 (d, J=8.4 Hz, 2H), 7.65 (d, J=8.4 Hz, 2H), 2.87 (s, 2H), 1.59 (s, 6H).

The synthesis of 6-(3-(4-bromophenyl)-1,2,4-oxadiazol-5-yl)-2,2-dimethyl-3,4-dihydro-2H-pyrano[2,3-b]pyridin-4-ol (171-2)

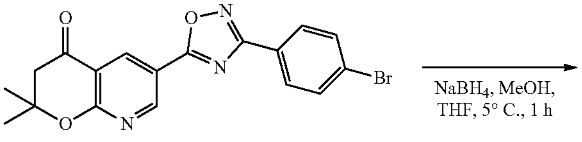

SMS21032-0142

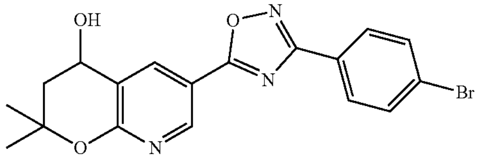

171-2

To a solution of SMS21032-0142 (70 mg, 0.17 mmol) in MeOH/THF (2 mL/2 mL) was added $NaBH_4$ (13.2 mg, 0.35 mmol) at 0° C., then the reaction mixture was stirred at 5° C. for another 1 h. After the reaction was complete (by LCMS), water (10 mL) and dichloromethane (10 mL) was added to the solution, the organic phase was separated, the water phase was extracted with dichloromethane (2×10 mL), the combined organic solution was washed with water then brine, dried over anhydrous $Na_2SO_4$, concentrated and purified by Prep-HPLC to give 171-2 (30 mg, yield: 43%) as a white solid.

The synthesis of (R)-6-(3-(4-bromophenyl)-1,2,4-oxadiazol-5-yl)-2,2-dimethyl-3,4-dihydro-2H-pyrano[2,3-b]pyridin-4-ol (SMS21032-0171) and (S)-6-(3-(4-bromophenyl)-1,2,4-oxadiazol-5-yl)-2,2-dimethyl-3,4-dihydro-2H-pyrano[2,3-b]pyridin-4-ol (SMS21032-0172)

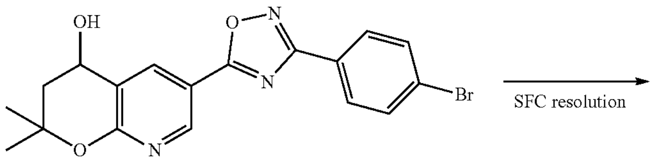

171-2

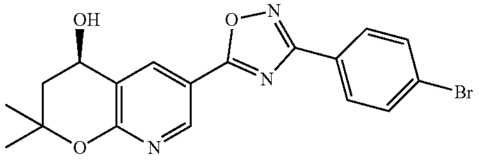

SMS21032-0171

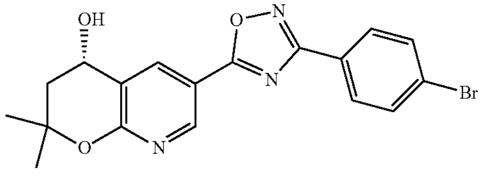

SMS21032-0172

SMS21032-0171 and SMS21032-0172 were separated by chiral HPLC using a CHIRALCEL OX-10 column (30×250 mm, 10 um) with MeOH as the mobile phase. The SMS21032-0171 (10 mg) was the first eluting compound and SMS21032-0172 (10 mg) was the second eluting compound.

SMS21032-0171

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity 100%, Rt=2.200 min; MS Calcd.: 401.0; MS Found: 402.0 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity 100%, Rt=10.607 min; MS Calcd.: 401.0; MS Found: 402.2 $[M+H]^+$.

$^1H$ NMR (400 MHz, $CDCl_3$) δ 8.92 (d, J=2.4 Hz, 1H), 8.55 (d, J=1.2 Hz, 1H), 7.95 (d, J=8.4 Hz, 2H), 7.57 (d, J=8.4 Hz, 2H), 4.90-4.99 (m, 1H), 2.33-2.48 (m, 1H), 2.25 (dd, J=13.6, 6.0 Hz, 1H), 1.86-1.92 (m, 1H), 1.52 (s, 3H), 1.36 (s, 3H).

SMS21032-0172

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity 100%, Rt=2.206 min; MS Calcd.: 401.0; MS Found: 402.0 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity 100%, Rt=10.599 min; MS Calcd.: 401.0; MS Found: 402.2 $[M+H]^+$.

$^1H$ NMR (400 MHz, $CDCl_3$) δ 9.00 (d, J=2.0 Hz, 1H), 8.62 (d, J=1.2 Hz, 1H), 8.02 (d, J=8.4 Hz, 2H), 7.65 (d, J=8.4 Hz, 2H), 4.97-5.07 (m, 1H), 2.39-2.48 (m, 1H), 2.32 (dd, J=13.2, 6.0 Hz, 1H), 1.93-1.99 (m, 1H), 1.59 (s, 3H), 1.44 (s, 3H).

Example 12: The synthesis of (R)-6-(3-(4-chlorophenyl)-1,2,4-oxadiazol-5-yl)-2,2-dimethyl-3,4-dihydro-2H-pyrano[2,3-b]pyridin-3-ol (SMS21032-0173-01)

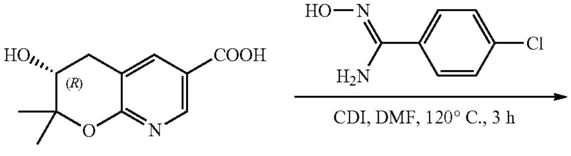

0097-5a

-continued

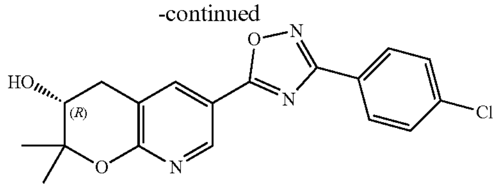

absolute stereochemistry
SMS21032-0173-01

To a stirred solution of compound 0097-5a (50 mg, 0.22 mmol) in DMF (5 ml) was added CDI (72 mg, 0.44 mmol). Stirred for 30 min at room temperature, then 4-chloro-N'-hydroxybenzimidamide (88 mg, 0.44 mmol) was added. The mixture was stirred for 3 h at 120° C. After the consumption of starting material (by LCMS), the reaction mixture was concentrated in vacuo, purified by prep-HPLC to give the product SMS21032-0173-01 (14 mg, 17.8% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 98.55%, Rt=2.191 min; MS Calcd.: 357.79; MS Found: 358.4 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.77%, Rt=10.470 min.

1H NMR (400 MHz, $CDCl_3$) δ 8.91 (d, J=2.0 Hz, 1H), 8.21 (d, J=1.6 Hz, 1H), 8.07 (d, J=8.4 Hz, 2H), 7.47 (d, J=8.4 Hz, 2H), 3.97 (t, J=4.4 Hz, 1H), 3.18-3.23 (m, 1H), 2.93-2.99 (m, 1H), 2.23 (s, 1H), 1.52 (s, 3H), 1.46 (s, 3H).

Example 13: The synthesis of (S)-6-(3-(4-chlorophenyl)-1,2,4-oxadiazol-5-yl)-2,2-dimethyl-3,4-dihydro-2H-pyrano[2,3-b]pyridin-3-ol (SMS21032-0174-01)

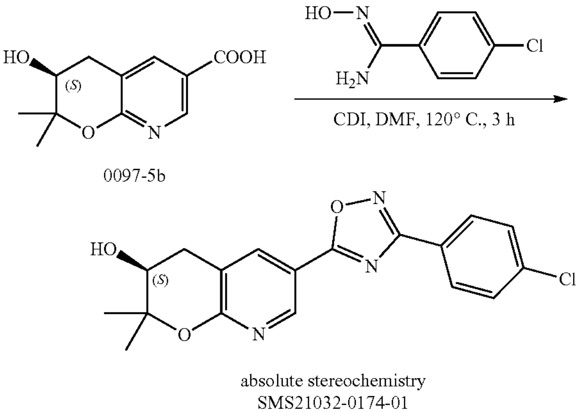

0097-5b absolute stereochemistry
SMS21032-0174-01

To a stirred solution of compound 0097-5b (60 mg, 0.27 mmol) in DMF (5 ml) was added CDI (88 mg, 0.54 mmol). Stirred for 30 min at room temperature, then 4-chloro-N'-hydroxybenzimidamide (96 mg, 0.54 mmol) was added. The mixture was stirred for 3 h at 120° C. After the consumption of starting material (by LCMS), the reaction mixture was concentrated in vacuo, purified by prep-HPLC to give the product SMS21032-0174-01 (21 mg, 21.8% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 98.47%, Rt=2.191 min; MS Calcd.: 357.79; MS Found: 358.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.79%, Rt=10.470 min.

$^1H$ NMR (400 MHz, $CDCl_3$) δ 8.95 (d, J=1.6 Hz, 1H), 8.22 (s, 1H), 8.09 (d, J=8.4 Hz, 2H), 7.49 (d, J=8.4 Hz, 2H), 3.97 (t, J=5.2 Hz, 1H), 3.18-3.23 (m, 1H), 2.93-2.99 (m, 1H), 1.97 (br, 1H), 1.51 (s, 3H), 1.46 (s, 3H.).

Example 14: The synthesis of (R)-2,2-dimethyl-6-(3-(thiazol-2-yl)-1,2,4-oxadiazol-5-yl)-3,4-dihydro-2H-pyrano[2,3-b]pyridin-3-ol (SMS21032-0182-01)

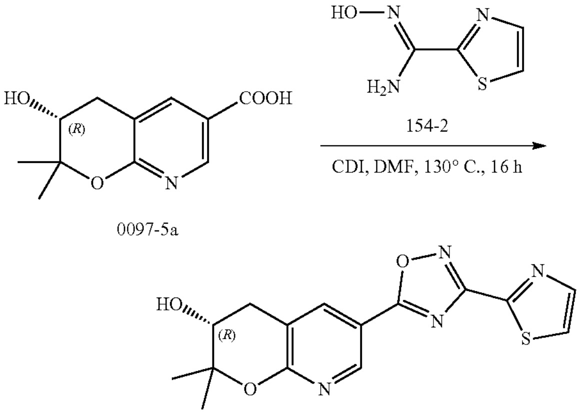

absolute stereochemistry
SMS21032-0182-01

To a stirred solution of compound 0097-5a (40 mg, 0.18 mmol) in DMF (5 ml) was added CDI (59 mg, 0.36 mmol). Stirred for 30 min at room temperature, then 154-2 (52 mg, 0.36 mmol) was added. The mixture was stirred for 16 h at 130° C. After the consumption of starting material (by LCMS), the reaction mixture was concentrated in vacuo, purified by prep-HPLC to give the product SMS21032-0182-01 (7.2 mg, 12% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 98.63%, Rt=1.598 min; MS Calcd.: 330.36; MS Found: 331.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 96.44%, Rt=7.244 min.

$^1H$ NMR (400 MHz, $CDCl_3$) δ 9.03 (d, J=2.4 Hz, 1H), 8.31-8.32 (m, 1H), 8.10 (d, J=3.2 Hz, 1H), 7.62 (d, J=3.2 Hz, 1H), 3.97 (t, J=5.2 Hz, 1H), 3.17-3.23 (m, 1H), 2.93-2.98 (m, 1H), 1.51 (s, 3H), 1.47 (s, 3H).

Example 15: The synthesis of 5-bromo-N'-hydroxy-thiophene-2-carboximidamide

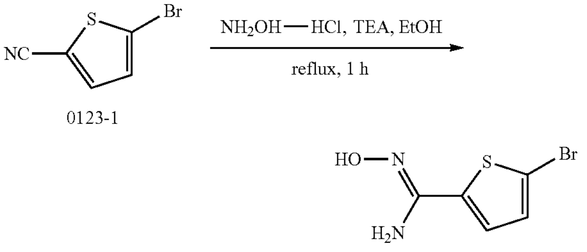

0123-2

To a stirred solution of compound 0123-1 (200 mg, 1.07 mmol) and hydroxylamine hydrochloride (150 mg, 2.14 mmol) in EtOH (10 ml) was added TEA (325 mg, 3.21 mmol). The mixture was refluxed for 1 h. After the consumption of starting material (by LCMS), the reaction solution was concentrated in vacuo. The residue was extracted with ethyl acetate, the combined organic phases were dried over anhydrous sodium sulfate, filtered, concentrated in vacuo to give the product 0123-2 (200 mg, 85% yield) as a white solid.

Example 16: The synthesis of (S)-2,2-dimethyl-6-(3-(thiazol-2-yl)-1,2,4-oxadiazol-5-yl)-3,4-dihydro-2H-pyrano[2,3-b]pyridin-3-ol (SMS21032-0183-01)

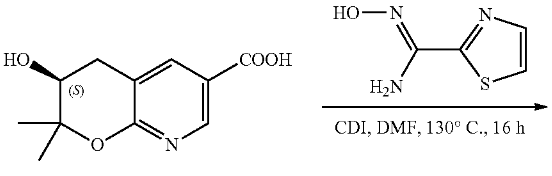

0097-5b

-continued

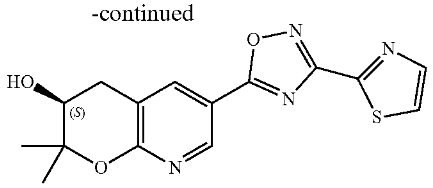

absolute stereochemistry
SMS21032-0183-01

To a stirred solution of compound 0097-5b (40 mg, 0.18 mmol) in DMF (5 ml) was added CDI (59 mg, 0.36 mmol). Stirred for 30 min at room temperature, then N'-hydroxythiazole-2-carboximidamide (52 mg, 0.36 mmol) was added. The mixture was stirred for 16 h at 130° C. After the consumption of starting material (by LCMS), the reaction mixture was concentrated in vacuo, purified by prep-HPLC to give the product SMS21032-0183-01 (22 mg, 37% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 99.02%, Rt=1.597 min; MS Calcd.: 330.36; MS Found: 331.4 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 94.10%, Rt=7.258 min.

$^1H$ NMR (400 MHz, $CDCl_3$) δ 9.03 (d, J=2.4 Hz, 1H), 8.30-8.31 (m, 1H), 8.10 (d, J=3.2 Hz, 1H), 7.62 (d, J=3.2 Hz, 1H), 3.97 (t, J=5.2 Hz, 1H), 3.17-3.23 (m, 1H), 2.92-2.98 (m, 1H), 1.50 (s, 3H), 1.47 (s, 3H)

Example 17: The synthesis of (R)-2,2-dimethyl-6-(3-(1-methyl-1H-pyrazol-3-yl)-1,2,4-oxadiazol-5-yl)-3,4-dihydro-2H-pyrano[2,3-b]pyridin-3-ol (SMS21032-0184-01)

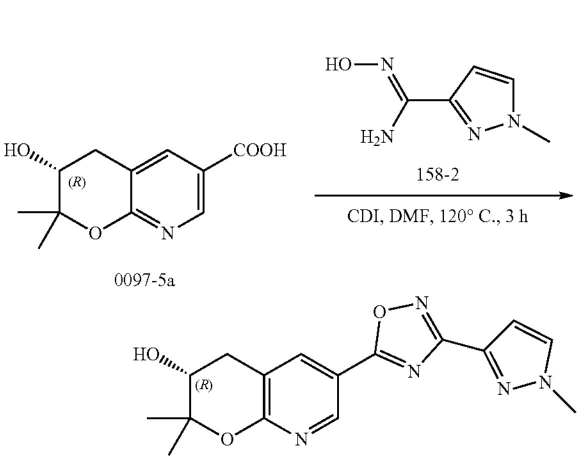

absolute stereochemistry
SMS21032-0184-01

To a stirred solution of compound 0097-5a (40 mg, 0.18 mmol) in DMF (5 ml) was added CDI (59 mg, 0.36 mmol). Stirred for 30 min at room temperature, then 158-2 (51 mg, 0.36 mmol) was added. The mixture was stirred for 3 h at 120° C. After the consumption of starting material (by LCMS), the reaction mixture was concentrated in vacuo, purified by prep-HPLC to give the product SMS21032-0184-01 (16 mg, 27% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 97.38%, Rt=1.492 min; MS Calcd.: 327.34; MS Found: 328.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=6.715 min.

$^1H$ NMR (400 MHz, $CDCl_3$) δ 9.03 (d, J=2.4 Hz, 1H), 8.31-8.32 (m, 1H), 7.49 (d, J=2.0 Hz, 1H), 6.90 (d, J=2.4 Hz, 1H), 4.05 (s, 3H), 3.96 (t, J=5.2 Hz, 1H), 3.15-3.21 (m, 1H), 2.90-2.96 (m, 1H), 1.49 (s, 3H), 1.46 (s, 3H).

Example 18: The synthesis of (S)-2,2-dimethyl-6-(3-(1-methyl-1H-pyrazol-3-yl)-1,2,4-oxadiazol-5-yl)-3,4-dihydro-2H-pyrano[2,3-b]pyridin-3-ol (SMS21032-0185-01)

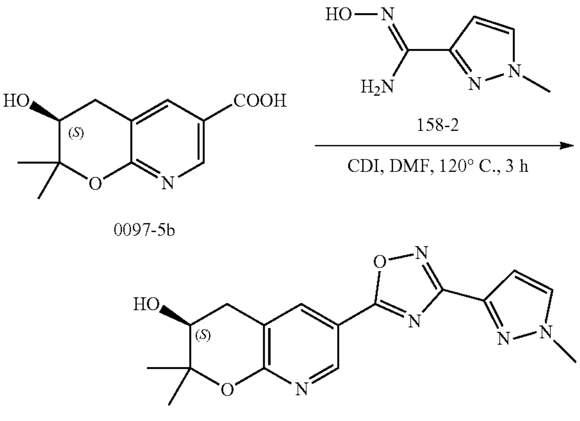

absolute stereochemistry
SMS21032-0185-01

To a stirred solution of compound 0097-5b (40 mg, 0.18 mmol) in DMF (5 ml) was added CDI (59 mg, 0.36 mmol). Stirred for 30 min at room temperature, then 158-2 (51 mg, 0.36 mmol) was added. The mixture was stirred for 3 h at 120° C. After the consumption of starting material (by LCMS), the reaction mixture was concentrated in vacuo, purified by prep-HPLC to give the product SMS21032-0185-01 (11 mg, 18.6% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 97.12%, Rt=1.492 min; MS Calcd.: 327.34; MS Found: 328.4 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=6.701 min.

$^1H$ NMR (400 MHz, $CDCl_3$) δ 9.03 (d, J=2.4 Hz, 1H), 8.30-8.31 (m, 1H), 7.49 (d, J=2.4 Hz, 1H), 6.90 (d, J=2.4 Hz, 1H), 4.05 (s, 3H), 3.93-3.98 (m, 1H), 3.15-3.21 (m, 1H), 2.90-2.96 (m, 1H), 1.90 (d, J=6.0 Hz, 1H), 1.49 (s, 3H), 1.46 (s, 3H).

Example 19: The synthesis of (S)-6-(3-(4-chlorophenyl)-1,2,4-oxadiazol-5-yl)-3-methoxy-2,2-dimethyl-3,4-dihydro-2H-pyrano[2,3-b]pyridine (SMS21032-0187-01)

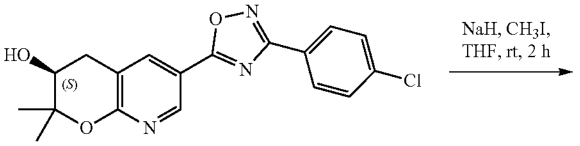

absolute stereochemistry
SMS21032-0174

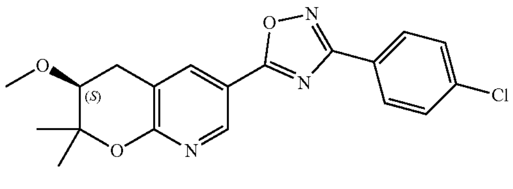

absolute stereochemistry
SMS21032-0187-01

To a stirred solution of compound SMS21032-0174 (60 mg, 0.17 mmol) and $CH_3I$ (121 mg, 0.85 mmol) in THF was slowly added NaH (13 mg, 0.51 mmol). The mixture was stirred at room temperature for 2 h. After the consumption of starting material (by LCMS), added water, the reaction solution was extracted with ethyl acetate, the combined organic phases were dried over anhydrous sodium sulfate, filtered, concentrated in vacuo, purified by prep-HPLC to give the product SMS21032-0187-01 (37 mg, 59% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 100%, Rt=2.461 min; MS Calcd.: 371.82; MS Found: 372.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=11.848 min.

$^1H$ NMR (400 MHz, $CDCl_3$) δ 8.97 (d, J=2.4 Hz, 1H), 8.23-8.24 (m, 1H), 8.09-8.11 (m, 2H), 7.48-7.51 (m, 2H), 3.47 (s, 3H), 3.44-3.45 (m, 1H), 3.14-3.19 (m, 1H), 2.93-2.99 (m, 1 H), 1.49 (s, 3H), 1.45 (s, 3H).

Example 20: The synthesis of (S)-6-(3-(4-fluorophenyl)-1,2,4-oxadiazol-5-yl)-2,2-dimethyl-3,4-dihydro-2H-pyrano[2,3-b]pyridin-3-ol (SMS21032-0190)

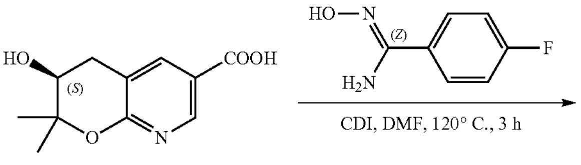

0097-5b

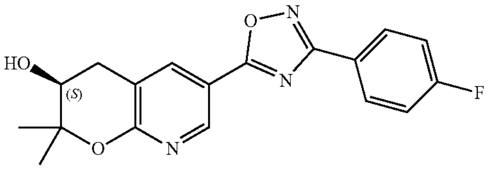

SMS21032-0190

To a solution of 0097-5b (120 mg, 0.54 mmol) in DMF (5 mL) was added CDI (174.39 mg, 1.08 mmol). The resulting solution was stirred at rt for 30 min and then (Z)-4-fluoro-N'-hydroxybenzimidamide (124.29 mg, 0.81 mmol) was added into this mixture. This mixture was heat to 120° C. for 3 h. After the consumption of starting material, the mixture was filtered and concentrated. The residue was purified by prep-HPLC to get SMS21032-0190 (43 mg, 23.41% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min, Purity: 99.10%, Rt=2.041 min; MS Found: 342.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min, Purity: 99.14%, Rt=9.643 min.

$^1H$ NMR (400 MHz, $CDCl_3$) δ 8.95 (d, J=2.4 Hz, 1H), 8.21-8.22 (m, 1H), 8.13-8.17 (m, 2H), 7.17-7.22 (m, 2H), 3.97 (s, 1H), 3.18-3.23 (m, 1H), 2.93-2.99 (m, 1H), 2.08 (s, 1H), 1.51 (s, 3H), 1.46 (s, 3H).

Example 21: The synthesis of N'-hydroxy-4-methylbenzimidamide (0191-2)

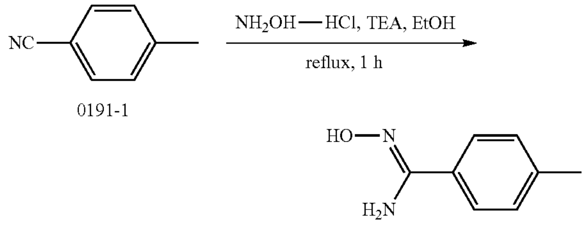

0191-1

0191-2

To a stirred solution of compound 0191-1 (500 mg, 4.27 mmol) and hydroxylamine hydrochloride (594 mg, 8.54 mmol) in EtOH (10 ml) was added TEA (1.3 g, 12.81 mmol). The mixture was refluxed for 1 h. After the consumption of starting material (by LCMS), the reaction solution was concentrated in vacuo. The residue was extracted with ethyl acetate, the combined organic phases were dried over anhydrous sodium sulfate, filtered, concentrated in vacuo to give the product 0191-2 (510 mg, 79.7% yield) as a light yellow liquid. The synthesis of (S)-2,2-dimethyl-6-(3-p-tolyl-1,2,4-oxadiazol-5-yl)-3,4-dihydro-2H-pyrano[2,3-b]pyridin-3-ol (SMS21032-0191-01).

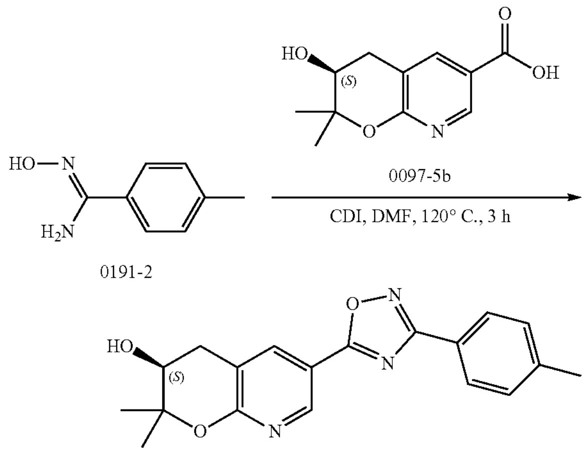

0097-5b 0191-2 absolute stereochemistry
SMS21032-0191-01

To a stirred solution of compound 0097-5b (50 mg, 0.23 mmol) in DMF (5 mL) was added CDI (75 mg, 0.46 mmol). Stirred for 30 min at room temperature, then 0191-2 (69 mg, 0.46 mmol) was added. The mixture was stirred for 3 h at 120° C. After the consumption of starting material (by LCMS), the reaction mixture was concentrated in vacuo, purified by prep-HPLC to give the product SMS21032-0191-01 (45 mg, 58% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 100%, Rt=2.155 min; MS Calcd.: 337.37; MS Found: 338.1 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.74%, Rt=10.194 min.

$^1H$ NMR (400 MHz, $CDCl_3$) δ 8.95 (d, J=2.0 Hz, 1H), 8.21-8.22 (m, 1H), 8.02 (d, J=8.0 Hz, 2H), 7.30 (d, J=8.0 Hz, 2H), 3.95 (t, J=5.2 Hz, 1H), 3.16-3.22 (m, 1H), 2.92-2.98 (m, 1H), 2.43 (s, 3H), 1.49 (s, 3H), 1.45 (s, 3H).

Example 22: The synthesis of (Z)-3,4-dichloro-N-hydroxybenzimidamide (0192-2)

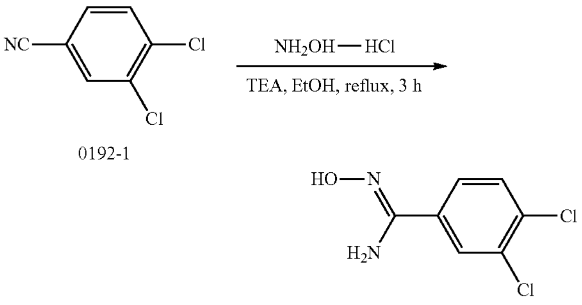

0192-1

0192-2

To a solution of 0192-1 (1 g, 5.81 mmol) in ethanol (15 ml) was added $NH_2OH$—HCl (808 mg, 11.63 mmol) and TEA (3.2 mL). The mixture was heated to reflux for 3 h. After the consumption of starting material (by LCMS), the solvent was removed, water (100 mL) was added, then extracted with dichloromethane, the combined organic phases were dried over anhydrous sodium sulfate, filtered, and concentrated in vacuo to give 0192-2 (600 mg, yield: 50%) as a white solid.

The synthesis of (S)-6-(3-(3,4-dichlorophenyl)-1,2,4-oxadiazol-5-yl)-2,2-dimethyl-3,4-dihydro-2H-pyrano[2,3-b]pyridin-3-ol (SMS21032-0192-01).

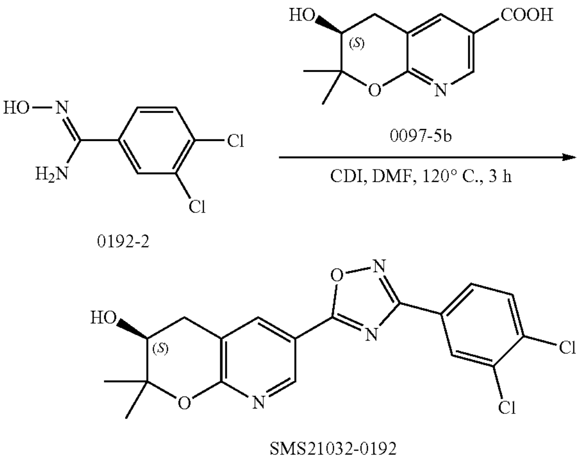

0097-5b 0192-2

SMS21032-0192

To a solution of compound 0097-5b (22 mg, 97.54 umol)) in DMF (4 mL) was added CDI (800 mg, 4.93 mmol). The mixture was stirred for about 30 min and then 0192-2 (40 mg, 185.08 umol) was added. The mixture was heated to 120° C. for 3 h. After cooling to rt, the mixture was extracted and purified by Prep-HPLC to give the desired product SMS21032-0192-01 (13 mg, yield: 33.8%) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 99.18%, Rt=2.359 min; MS Calcd.: 391.1; MS Found: 392.2 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 99.38%, Rt=11.393 min.

$^1H$ NMR (400 MHz, DMSO-$d_6$) δ 8.83 (d, J=2.4 Hz, 1H), 8.33 (d, J=2.0 Hz, 1H), 8.26 (d, J=2.0 Hz, 1H), 8.06 (dd, J=8.4 Hz, 2.0 Hz, 1H), 7.90 (d, J=8.4 Hz, 1H), 5.40 (d, J=4.8 Hz, 1H), 3.76-3.80 (m, 1H), 3.13 (dd, J=16.8 Hz, 4.8 Hz, 1H), 2.83 (dd, J=17.2 Hz, 6.0 Hz, 1H), 1.34 (s, 6H).

Example 23: The synthesis of (S)-6-(3-(5-chlorothiazol-2-yl)-1,2,4-oxadiazol-5-yl)-2,2-dimethyl-3,4-dihydro-2H-pyrano[2,3-b]pyridin-3-ol (SMS21032-0193)

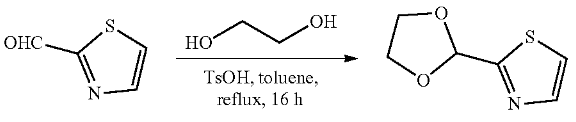

193-1

To the solution of ethylene glycol (2.2 g, 35.36 mmol), thiazole-2-carbaldehyde (2.0 g, 17.68 mmol) in toluene (20 mL) was added TsOH (92.08 mg, 1.77 mmol), then the mixture was refluxed for 16 h. Diluted with EA (50 mL), washed with brine (50 mL), dried in $Na_2SO_4$. Filtration and concentrated the filtrate to give 193-1 (2.5 g, yield: 90%) as yellow liquid.

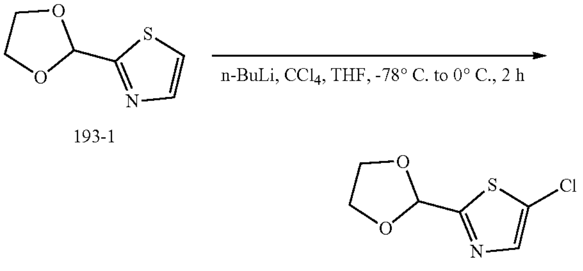

193-1

193-2

To the solution of 193-1 (1 g, 6.36 mmol) in THF (20 mL) was added n-BuLi (3.1 mL, 2.5 M in hexane) dropwise at −78° C., when addition was completed, the mixture was stirred at −78° C. for 30 min, then $CCl_4$ (3.1 mL) was added in 5 min dropwise, then the mixture was stirred at 0° C. for 2 h. Quenched with water (20 ml), extracted by EA (35 mL*2), EA phase was dried in $Na_2SO_4$. Filtration and concentrated the filtrate to oil, purified by CC (EA:PE=1:4) to give 193-2 (0.9 g, yield: 75%) as yellow liquid.

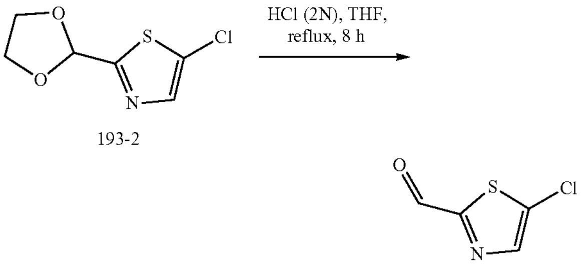

193-2

193-3

To the solution of 193-2 (0.91 g, 4.75 mmol) in THF (10 mL) was added HCl (2N, 5 mL), then the mixture was refluxed for 8 h. EA (40 mL) was added, washed with water (30 mL), sat $NaHCO_3$ (40 mL*2), dried in $Na_2SO_4$. Filtration and concentrated the filtrate to oil, purified by CC (EA:PE=1:10) to give 193-3 (0.35 g, yield: 50%) as yellow liquid.

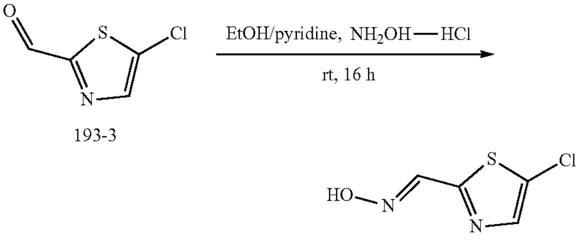

193-3

193-4

To the solution of 193-3 (350 mg, 2.37 mmol) in EtOH (10 mL) was added Hydroxylamine hydrochloride (247 mg, 3.56 mmol), Pyridine (1.88 g, 23.72 mmol) at room temperature, then the mixture was stirred at room temperature for 16 h. Concentrated to oil, diluted with EA (20 mL), then washed by brine (15 mL), dried in $Na_2SO_4$. Filtration and concentrated the filtrate to give 193-4 (371 mg, yield: 96%) as a brown solid.

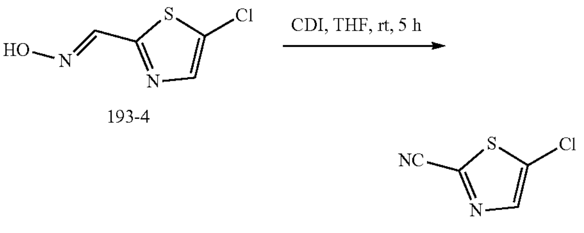

193-4

193-5

To the solution of 193-4 (340 mg, 2.09 mmol) in THF (3 mL) was added CDI (452 mg, 3.14 mmol) at room temperature, then the mixture was stirred at room temperature for 5 h. Diluted with EA (40 mL), washed by brine (20 mL), dried in $Na_2SO_4$. Filtration and concentrated the filtrate to give 193-5 (250 mg, yield: 83%) as yellow oil.

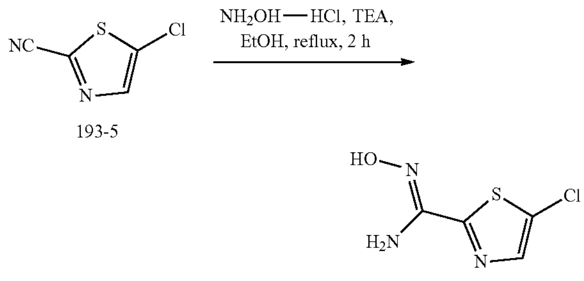

193-5

193-6

To the solution of 193-5 (250 mg, 1.73 mmol) in EtOH (15 mL) was added Hydroxylamine hydrochloride (144 mg, 2.07 mmol), TEA (700 mg, 6.92 mmol, 964.02 uL), then mixture was refluxed for 2 h. Concentrated to solid, diluted with EA (80 mL), washed by water (10 mL), dried in $Na_2SO_4$. Filtration and concentrated the filtrate to give 193-6 (235 mg, yield: 77%) as a brown solid.

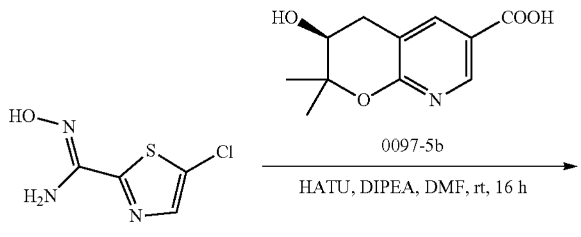

0097-5b 193-6

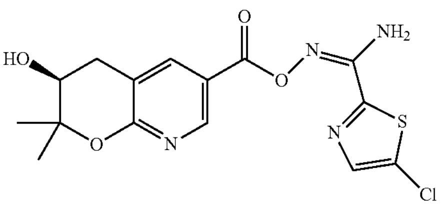

193-7

To the solution of 0097-5b (60 mg, 269 umol) in DMF (3 mL) was added HATU (112 mg, 296 umol) at room temperature, then 193-6 (53 mg, 296 umol) DIPEA (52 mg, 403 umol) were added, the mixture was stirred at room temperature for 16 h. Diluted with water (20 mL), extracted with EA (20 mL), the EA phase was washed with brine (20 mL), dried in $Na_2SO_4$. Filtration and concentrated to give 193-7 (70 mg, yield: 68%) as yellow oil.

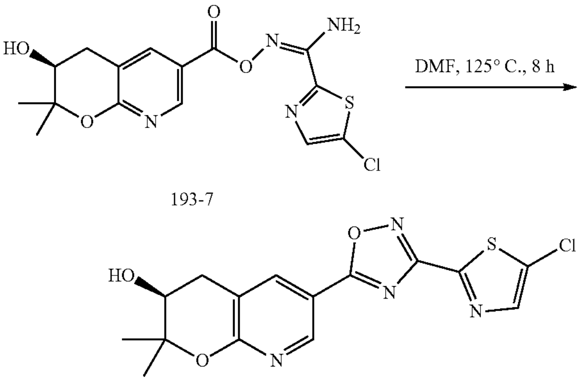

193-7

SMS21032-0193

The solution of 193-7 (24 mg, 62.69 umol) in DMF (3 mL) was heated to 125° C. for 8 h. Diluted with water (10 mL), extracted with EA (20 mL), the EA phase was washed with brine (20 mL), dried in $Na_2SO_4$. Filtration and concentrated to oil, purified by Prep-HPLC to give SMS21032-0193 (8 mg, yield: 35%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=1.866 min; MS Calcd: 364.0; MS Found: 365.0 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=8.528 min.

MS Calcd: 364.0; MS Found: 365.2 $[M+H]^+$.

$^1H$ NMR (400 MHz, $CDCl_3$) δ 9.00 (d, J=2.4 Hz, 1H), 8.26-8.29 (m, 1H), 7.88 (s, 1H), 3.94-3.99 (m, 1H), 3.19 (dd, J=16.8, 4.8 Hz, 1H), 2.95 (dd, J=17.0, 5.8 Hz, 1H), 1.92 (d, J=6.0 Hz, 1H), 1.50 (s, 3H), 1.47 (s, 3H).

Example 24: The synthesis of (S)-2,2-dimethyl-6-(3-(5-methylthiazol-2-yl)-1,2,4-oxadiazol-5-yl)-3,4-dihydro-2H-pyrano[2,3-b]pyridin-3-ol (SMS21032-0194)

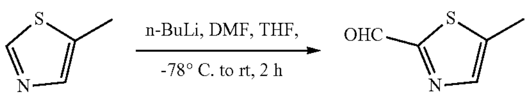

194-1

To the solution of 5-methylthiazole (500 mg, 5.0 mmol) in THF (5 mL) was added n-BuLi (2 mL) dropwise at −78° C., then the mixture was stirred at −78° C. for 10 min, DMF (553 mg, 7.6 mmol) was added, the mixture was stirred at −78° C. for 10 min, then warmed to room temperature and stirred for 2 h. Quenched by sat $NH_4Cl$, extracted with EA (30 mL), EA phase was dried in $Na_2SO_4$. Filtration and concentrated the filtrate to oil, purified by CC (EA:PE=1:8) to give 194-1 (32 mg, yield: 50%) as yellow oil.

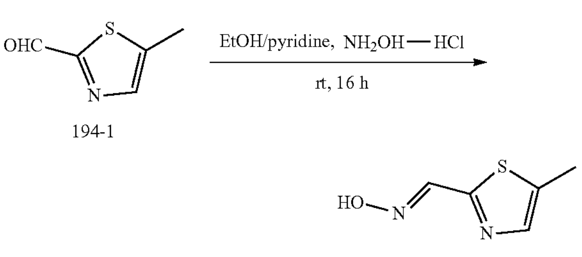

194-1

194-2

To the solution of 194-1 (50 mg, 393 umol) in EtOH (1 mL) was added Pyridine (0.2 mL), Hydroxylamine hydrochloride (55 mg, 786 umol) at room temperature, then the mixture was stirred at room temperature for 16 h. Diluted with water (10 mL), extracted by EA (15 mL*2), EA phase was dried in $Na_2SO_4$. Filtration and concentrated the filtrate to give 194-2 (51 mg, yield: 91%) as a white solid.

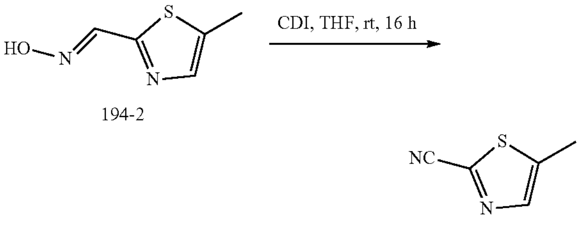

194-2

194-3

To the solution of 194-2 (50 mg, 352 umol) in DCM (3 mL) was added CDI (68 mg, 422 umol), then the mixture was stirred at room temperature for 16 h. Diluted with water (10 mL), extracted with DCM (20 mL), dried in $Na_2SO_4$. Filtration and concentrated to give 194-3 (30 mg, yield: 69%) as yellow liquid.

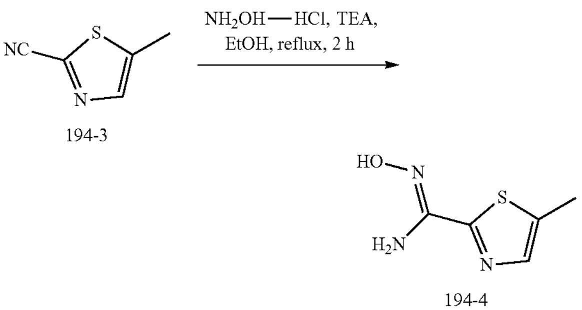

194-3

194-4

To the solution of 194-3 (40 mg, 322 umol) in EtOH (5 mL) was added Hydroxylamine hydrochloride (45 mg, 644 umol), TEA (33 mg, 322 umol), then the mixture was refluxed for 2 h. Concentrated to solid, Diluted with EA (10 mL), then filtration and the solid was washed by EA, the filtrate was concentrated to give 194-4 (25 mg, yield: 49%) as a white solid.

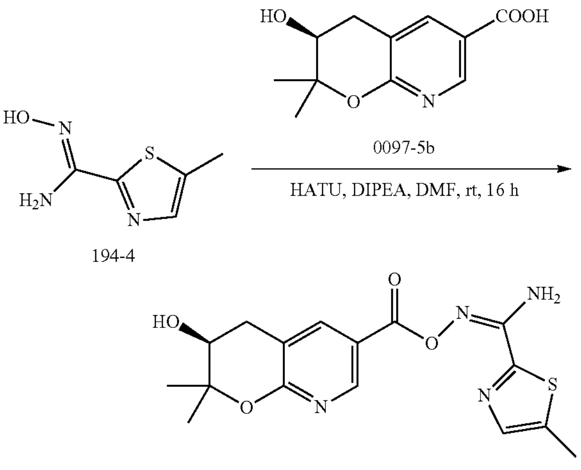

194-4

194-5

To the solution of 0097-5b (60 mg, 269 umol) in DMF (1 mL) was added HATU (112 mg, 296 umol) at room temperature, then 194-4 (47 mg, 296 umol), DIPEA (52 mg, 403 umol) was added, the mixture was stirred at room temperature for 16 h. Diluted with water (10 mL), extracted with EA (20 mL), the EA phase was washed with brine (20 mL), dried in $Na_2SO_4$. Filtration and concentrated to give 194-5 (80 mg, yield: 82%) as yellow oil.

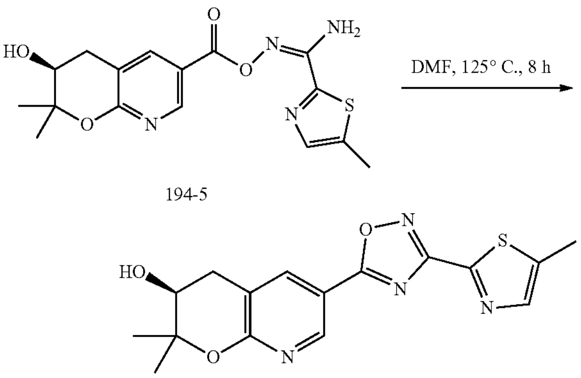

194-5

SMS21032-0194

The solution of 194-5 (80 mg, 221 umol) in DMF (2 mL) was heated to 125° C. for 8 h. Diluted with water (10 mL), extracted with EA (20 mL), the EA phase was washed with brine (20 mL), dried in $Na_2SO_4$. Filtration and concentrated to oil, purified by Prep-HPLC to give SMS21032-0194 (10 mg, yield: 13%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=1.705 min; MS Calcd: 344.1; MS Found: 345.1 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=7.587 min.

MS Calcd: 344.1; MS Found: 345.2 $[M+H]^+$.

$^1H$ NMR (400 MHz, $CDCl_3$) δ 9.01 (d, J=2.4 Hz, 1H), 8.28-8.30 (m, 1H), 7.74 (d, J=1.2 Hz, 1H), 3.93-3.99 (m, 1H), 3.19 (dd, J=17.2, 4.8 Hz, 1H), 2.94 (dd, J=17.0, 5.8 Hz, 1H), 2.60 (d, J=1.2 Hz, 3H), 1.95 (d, J=6.0 Hz, 1H), 1.50 (s, 3H), 1.46 (s, 3H).

Example 25: The synthesis of (R)-6-(3-(5-chlorothiazol-2-yl)-1,2,4-oxadiazol-5-yl)-2,2-dimethyl-3,4-dihydro-2H-pyrano[2,3-b]pyridin-3-ol (SMS21032-0197)

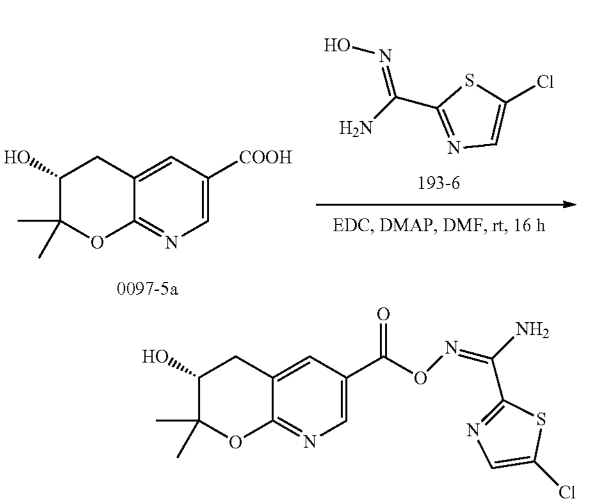

193-6

0097-5a 197-1

0097-5a (50 mg, 224 umol) in DMF (3 mL) was added EDC (56 mg, 291 umol) DMAP (3 mg, 22 umol) at room temperature, then 193-6 (44 mg, 246 umol) was added, the mixture was stirred at room temperature for 16 h. Diluted with water (20 mL), extracted with EA (20 mL), the EA phase was washed with brine (20 mL), dried in $Na_2SO_4$. Filtration and concentrated to give 197-1 (55 mg, yield: 64%) as yellow oil.

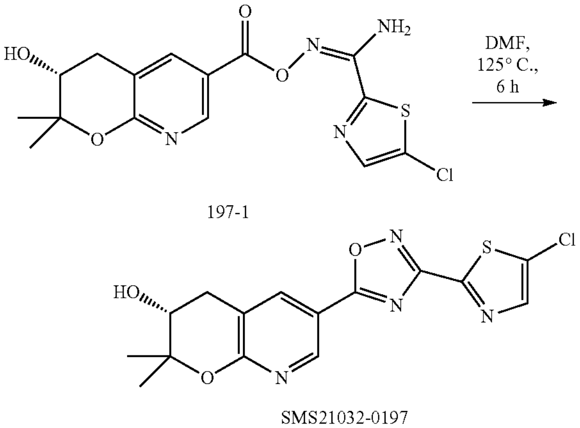

197-1

SMS21032-0197

The solution of 197-1 (55 mg, 144 umol) in DMF (2 mL) was heated to 125° C. for 6 h.

Diluted with water (10 mL), extracted with EA (20 mL), the EA phase was washed with brine (20 mL), dried in $Na_2SO_4$. Filtration and concentrated to oil, purified by Prep-HPLC to give SMS21032-0197 (10 mg, yield: 19%) as a yellow solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=1.909 min; MS Calcd: 364.0; MS Found: 365.1 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=8.516 min.

MS Calcd: 364.0; MS Found: 365.2 $[M+H]^+$.

$^1H$ NMR (400 MHz, $CDCl_3$) δ 8.92 (d, J=2.0 Hz, 1H), 8.19-8.22 (m, 1H), 7.81 (s, 1H), 3.87-3.92 (m, 1H), 3.12 (dd, J=17.0, 4.6 Hz, 1H), 2.88 (dd, J=17.2, 6.0 Hz, 1H), 1.90 (d, J=6.0 Hz, 1H), 1.43 (s, 3H), 1.40 (s, 3H).

Example 26: The synthesis of (R)-2,2-dimethyl-6-(3-(5-methylthiazol-2-yl)-1,2,4-oxadiazol-5-yl)-3,4-dihydro-2H-pyrano[2,3-b]pyridin-3-ol (SMS21032-0198)

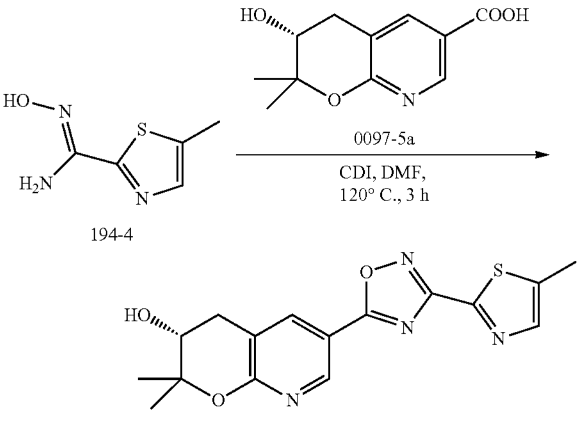

0097-5a 194-4

SMS21032-0198

To the solution of 0097-5a (50 mg, 224 umol) in DMF (5 mL) was added CDI (44 mg, 269 umol), then 194-4 (35 mg, 224 umol) was added, the mixture was heated to 120° C. for 3 h. Diluted with water (10 mL), extracted with EA (20 mL), the EA phase was washed with brine (20 mL), dried in $Na_2SO_4$. Filtration and concentrated to oil, purified by Prep-HPLC to give SMS21032-0198 (7 mg, yield: 9%) as a white solid.

Agilent LCMS 1200-6110, Column: Waters X-Bridge C18 (50 mm*4.6 mm*3.5 m); Column Temperature: 40° C.; Flow Rate: 2.0 mL/min; Mobile Phase: from 95% [water+

0.05% TFA] and 5% [CH3CN+0.05% TFA] to 0% [water+0.05% TFA] and 100% [CH3CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity: 99.6%, Rt=1.583 min; MS Calcd: 344.1; MS Found: 345.3 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=7.548 min.

MS Calcd: 344.1; MS Found: 345.2 $[M+H]^+$.

$^1H$ NMR (400 MHz, $CDCl_3$) δ 9.01 (d, J=2.4 Hz, 1H), 8.28-8.31 (m, 1H), 7.74 (d, J=1.2 Hz, 1H), 3.94-3.99 (m, 1H), 3.19 (dd, J=17.2, 4.8 Hz, 1H), 2.94 (dd, J=17.0, 5.8 Hz, 1H), 2.60 (d, J=0.8 Hz, 3H), 1.92 (d, J=6.0 Hz, 1H), 1.50 (s, 3H), 1.46 (s, 3H).

Example 27: The synthesis of (R)-6-(3-(4-chlorothiazol-2-yl)-1,2,4-oxadiazol-5-yl)-2,2-dimethyl-3,4-dihydro-2H-pyrano[2,3-b]pyridin-3-ol (SMS21032-0199)

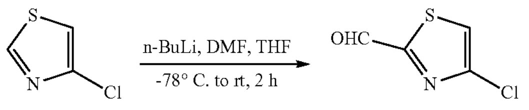

199-1

To the solution of 4-chlorothiazole (1.0 g, 8.36 mmol) in THF (15 mL) was added n-BuLi (4 mL) dropwise at −78° C., then the mixture was stirred at −78° C. for 10 min, DMF (673 mg, 9.20 mmol) was added, the mixture was stirred at −78° C. for 10 min, then warmed to room temperature and stirred for 2 h. Quenched with water (20 mL), extracted by EA (35 mL*2), EA phase was dried in $Na_2SO_4$. Filtration and concentrated the filtrate to oil, purified by CC (EA: PE=1:10) to give 199-1 (371 mg, yield: 30%) as white solid.

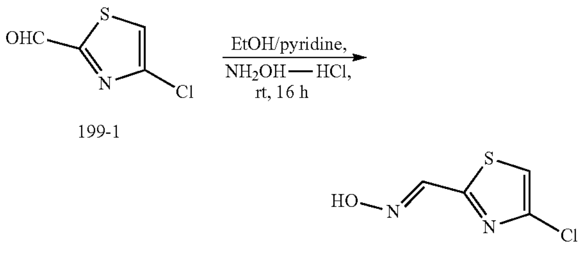

199-1

199-2

To the solution of 199-1 (370 mg, 2.51 mmol) in EtOH (10 mL) was added Hydroxylamine hydrochloride (261 mg, 3.76 mmol), Pyridine (1.98 g, 25.07 mmol) at room temperature, then the mixture was stirred at room temperature for 16 h. Concentrated to oil, diluted with EA (50 mL), then washed by brine (25 mL), dried in $Na_2SO_4$. Filtration and concentrated the filtrate to give 199-2 (270 mg, yield: 66%) as a white solid.

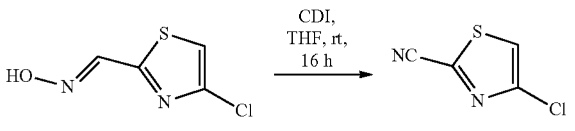

199-2 199-3

To the solution of 199-2 (240 mg, 1.48 mmol) in THF (10 mL) was added CDI (359 mg, 2.21 mmol), then mixture was stirred at room temperature for 16 h. Diluted with EA (35 mL), washed by brine (20 mL), dried in $Na_2SO_4$. Filtration and concentrated the filtrate to give 199-3 (200 mg, yield: 94%) as yellow liquid.

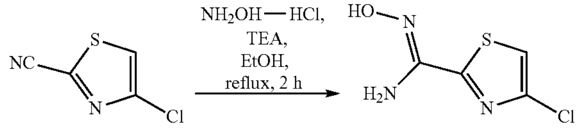

199-3 199-4

To the solution of 199-3 (200 mg, 1.38 mmol) in EtOH (10 mL) was added Hydroxylamine hydrochloride (115 mg, 1.66 mmol), TEA (560 mg, 5.53 mmol), then mixture was refluxed for 2 h. Concentrated to solid, diluted with EA (80 mL), washed with water (10 mL), EA phase was dried in $Na_2SO_4$. Filtration and concentrated the filtrate to give 199-4 (210 mg, yield: 85%) as a yellow solid.

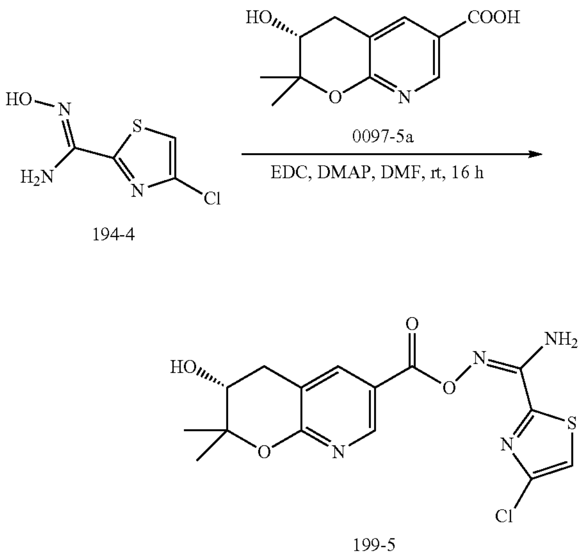

194-4

199-5

To the solution of 0097-5a (60 mg, 269 umol) in DMF (1 mL) was added EDC (62 mg, 323 umol), DMAP (3 mg, 27 umol) at room temperature, the mixture was stirred at room temperature for 15 min, then 199-4 (46 mg, 296 umol) was added, the mixture was stirred at room temperature for 16 h. Diluted with water (10 mL), extracted with EA (20 mL), the EA phase was washed with brine (20 mL), dried in $Na_2SO_4$. Filtration and concentrated to give 199-5 (65 mg, yield: 67%) as yellow oil.

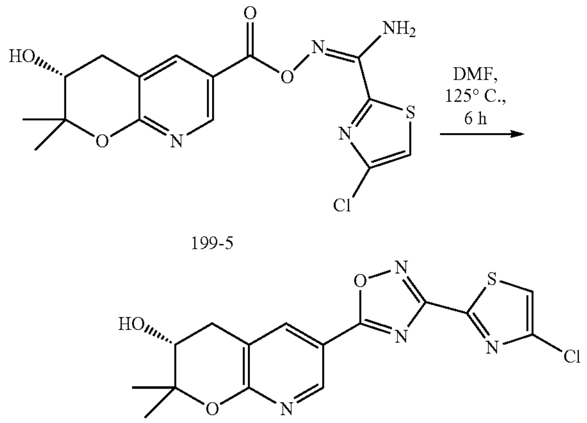

199-5

SMS21032-0199

The solution of 199-5 (65 mg, 179 umol) in DMF (3 mL) was heated to 125° C. for 6 h. Diluted with water (10 mL), extracted with EA (20 mL), the EA phase was washed with brine (20 mL), dried in $Na_2SO_4$. Filtration and concentrated to oil, purified by Prep-HPLC to give SMS21032-0199 (10 mg, yield: 16%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=1.826 min; MS Calcd: 364.0; MS Found: 365.0 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=8.140 min. MS Calcd: 364.0; MS Found: 365.2 $[M+H]^+$.

$^1H$ NMR (400 MHz, $CDCl_3$) δ 8.93 (d, J=2.4 Hz, 1H), 8.20-8.23 (m, 1H), 7.31 (s, 1H), 3.86-3.93 (m, 1H), 3.13 (dd, J=17.0, 4.6 Hz, 1H), 2.88 (dd, J=17.0, 5.8 Hz, 1H), 1.89 (d, J=6.0 Hz, 1H), 1.44 (s, 3H), 1.40 (s, 3H).

Example 28: The synthesis of (S,E)-4-chloro-N'-(3-hydroxy-2,2-dimethyl-3,4-dihydro-2H-pyrano[2,3-b]pyridine-6-carbonyloxy)thiazole-2-carboximidamide (200-1)

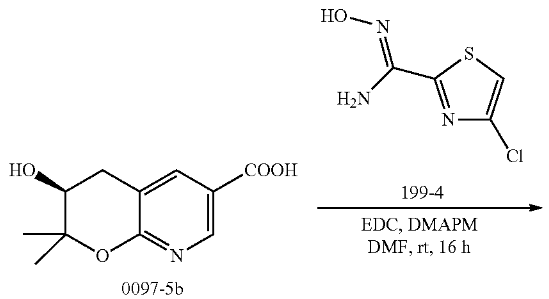

0097-5b

-continued

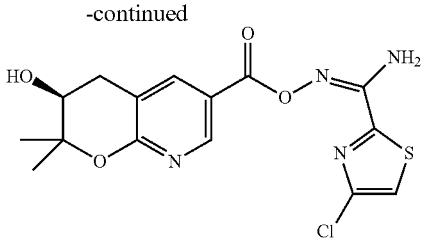

200-1

To the solution of 0097-5b (60 mg, 269 umol) in DMF (1 mL) was added EDC (62 mg, 323 umol), DMAP (3 mg, 27 umol) at room temperature, the mixture was stirred at room temperature for 15 min, then 199-4 (46 mg, 296 umol) was added, the mixture was stirred at room temperature for 16 h. Diluted with water (10 mL), extracted with EA (20 mL), the EA phase was washed with brine (20 mL), dried in $Na_2SO_4$. Filtration and concentrated to give 200-1 (60 mg, yield: 62%) as yellow oil.

The synthesis of (S)-6-(3-(4-chlorothiazol-2-yl)-1,2,4-oxadiazol-5-yl)-2,2-dimethyl-3,4-dihydro-2H-pyrano[2,3-b]pyridin-3-ol (SMS21032-0200)

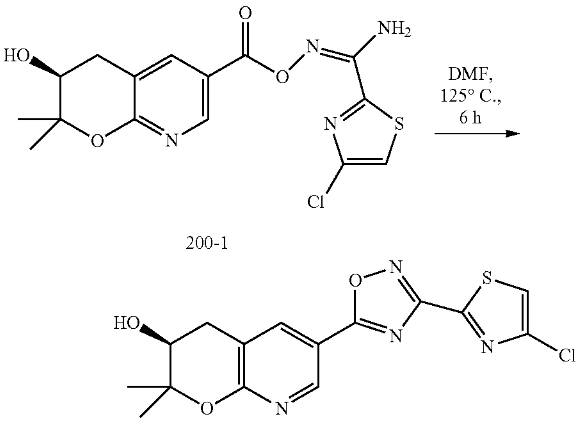

200-1

SMS21032-0200

The solution of 199-5 (60 mg, 165 umol) in DMF (3 mL) was heated to 125° C. for 6 h. Diluted with water (10 mL), extracted with EA (20 mL), the EA phase was washed with brine (20 mL), dried in $Na_2SO_4$. Filtration and concentrated to oil, purified by Prep-HPLC to give SMS21032-0200 (9 mg, yield: 16%) as a white solid.

LC-MS (Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=1.833 min; MS Calcd: 364.0; MS Found: 365.0 $[M+H]^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 100%, Rt=8.135 min.

MS Calcd: 364.0; MS Found: 365.2 [M+H]$^+$.

$^1$H NMR (400 MHz, $CDCl_3$) δ 9.00 (d, J=2.0 Hz, 1H), 8.27-8.30 (m, 1H), 7.38 (s, 1H), 3.94-3.99 (m, 1H), 3.20 (dd, J=17.0, 4.6 Hz, 1H), 2.95 (dd, J=17.0, 5.8 Hz, 1H), 1.91 (d, J=5.6 Hz, 1H), 1.50 (s, 3H), 1.47 (s, 3H).

Example 29: The synthesis of 1-ethyl-1H-pyrazole-3-carbonitrile (201-1)

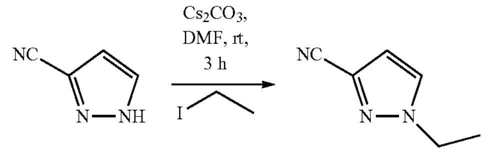

201-0 201-1

To a stirred solution of 201-0 (1.0 g, 10.74 mmol) in DMF (10 mL) was added iodoethane (2.01 g, 12.89 mmol) and $Cs_2CO_3$ (6.99 g, 21.48 mmol). The mixture was stirred at rt for 3 h. After the reaction was completed, the mixture was quenched with water and then extracted with EA (30 mL×3). The organic layer was separated, dried over $Na_2SO_4$ and concentrated in vacuo. The residue was purified by column chromatography (petrol ether/EtOAc=1/1) to get 201-1 (1.1 g, 84.62% yield) as a white solid.

The synthesis of (Z)-1-ethyl-N'-hydroxy-1H-pyrazole-3-carboximidamide (201-2)

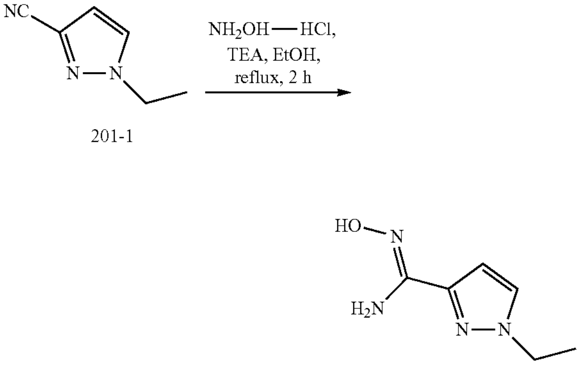

201-1

201-2

To a solution of 201-1 (1.1 g, 9.08 mmol) in EtOH (10 mL) was added $NH_2OH$—HCl (946.45 mg, 13.62 mmol) and TEA (2.76 g, 27.24 mmol). The resulting reaction mixture was stirred at 80° C. for 2 h. Then added water (30 mL), the aqueous phase was extracted with ethyl acetate (40 mL×3), the combined organic phases were washed with water (50 mL×3) and dried over anhydrous sodium sulfate, filtered, and concentrated in vacuo to get 201-2 (1.3 g, 92.92% yield) as a white solid.

The synthesis of (R)-6-(3-(1-ethyl-1H-pyrazol-3-yl)-1,2,4-oxadiazol-5-yl)-2,2-dimethyl-3,4-dihydro-2H-pyrano[2,3-b]pyridin-3-ol (SMS21032-0201)

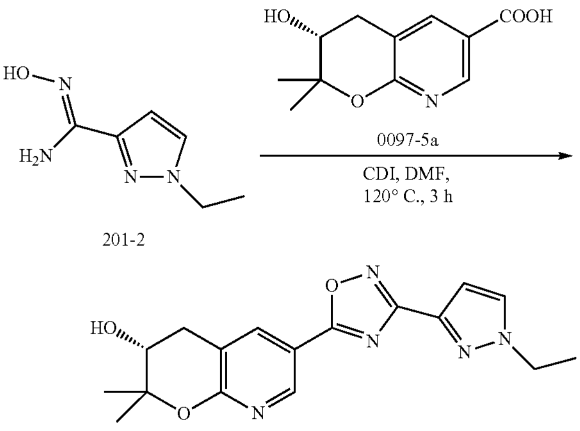

201-2

SMS21032-0201

To a solution of 0097-5a (50 mg, 223.98 umol) in DMF (5 mL) was added CDI (72.63 mg, 447.96 umol) and 201-2 (51.80 mg, 335.97 umol). The resulting solution was stirred at rt for 30 min and then this mixture was heat to 120° C. for 3 h. After the consumption of starting material, the mixture was filtered. The residue was purified by prep-HPLC to get SMS21032-0201 (20.5 mg, 26.81% yield) as a white solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min, Purity: 99.62%, Rt=1.660 min; MS Found: 342.3 [M+H]$^+$.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min, Purity: 100%, Rt=7.583 min.

$^1$H NMR (400 MHz, $CDCl_3$) δ 9.01 (d, J=2.4 Hz, 1H), 8.29-8.30 (m, 1H), 7.51 (d, J=2.4 Hz, 1H), 6.89 (d, J=2.0 Hz, 1H), 4.32 (q, J=7.2 Hz, 2H), 3.94 (t, J=5.6 Hz, 1H), 3.17 (dd, J=11.6 Hz, J=5.2 Hz, 1H), 2.92 (dd, J=16.8 Hz, J=6.0 Hz, 1H), 2.00 (br, 1H), 1.54 (t, J=7.2 Hz, 3H), 1.47 (d, J=12.8 Hz, 6H).

Example 30: The synthesis of (S)-6-(3-(3-chlorophenyl)-1,2,4-oxadiazol-5-yl)-2,2-dimethyl-3,4-dihydro-2H-pyrano[2,3-b]pyridin-3-ol (SMS21032-0211-01)

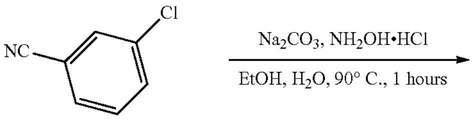

-continued

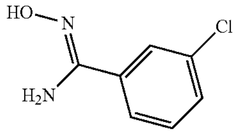

0211-1

To a mixture of 3-chlorobenzonitrile (500.0 mg, 3.63 mmol, 438.60 uL) and $NH_2OH{\cdot}HCl$ (1.00 g, 14.54 mmol) in EtOH (10 mL) and $H_2O$ (5 mL) was added $Na_2CO_3$ (847.59 mg, 8.00 mmol). The mixture was stirred at 90° C. for 1 hr. LCMS indicated the NBK0071-2-R1 was consumed completely. The purity on LCMS was ~87%. The mixture was filtered and the filtrate was concentrated in vacuo. 3-chloro-N'-hydroxy-benzamidine (1.65 g, 3.63 mmol, 99.79% yield, 37.5% purity) was obtained as a light yellow solid was obtained. Some salts were remained in it. The product was used to the next step reaction without any purification.

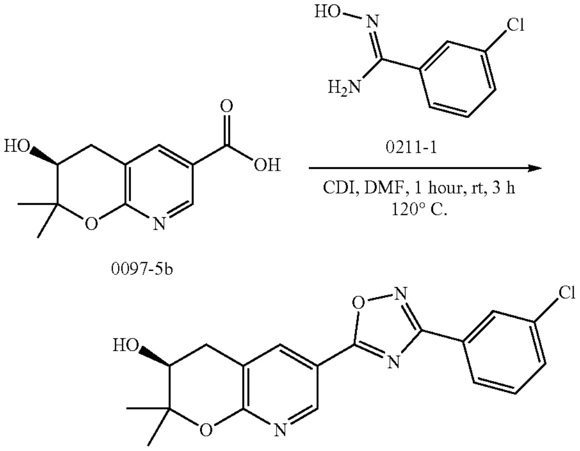

0097-5b

SMS21032-0211-01

A mixture of (3S)-3-hydroxy-2,2-dimethyl-3,4-dihydropyrano[2,3-b]pyridine-6-carboxylic acid (60.0 mg, 268.79 umol) in DMF (3 mL) was added CDI (77.38 mg, 537.57 umol). The mixture was stirred at 20° C. for 1 hour. Then 3-chloro-N'-hydroxy-benzamidine (244.56 mg, 537.57 umol) was added to the above mixture. The temperature was warmed up to 120° C. and stirred at this temperature for 3 hr. LCMS (NBK0071-6-P1-1) showed the desired product was generated. The mixture was combined with NBK0071-4. The mixture was filtered and the filtration was purified by Prep. HPLC. (3S)-6-[3-(3-chlorophenyl)-1,2,4-oxadiazol-5-yl]-2,2-dimethyl-3,4-dihydropyrano[2,3-b]pyridin-3-ol (38 mg, 106.21 umol, 100% purity) as a light yellow solid was obtained. Yield: 29.6% Agilent LCMS 21500-6120, Column: Waters X-Bridge C18 (50 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 96.35%, Rt=1.942 min; MS Found: 357.8 $[M+H]^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM NH4HCO3] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 99.85%, Rt=10.279 min.

$^1H$ NMR (400 MHz, $CDCl_3$) δ 8.95 (d, J=2.3 Hz, 1H), 8.26-8.19 (m, 1H), 8.15 (t, J=1.7 Hz, 1H), 8.04 (dt, J=7.5, 1.3 Hz, 1H), 7.53-7.40 (m, 2H), 3.97 (dd, J=10.9, 5.8 Hz, 1H), 3.21 (dd, J=17.0, 4.8 Hz, 1H), 2.96 (dd, J=17.0, 5.7 Hz, 1H), 2.01 (d, J=6.2 Hz, 1H), 1.51 (s, 3H), 1.46 (s, 3H). ESI-MS (M+H+): 357.8

Example 31: The synthesis of (R)-6-(3-(3-chlorophenyl)-1,2,4-oxadiazol-5-yl)-2,2-dimethyl-3,4-dihydro-2H-pyrano[2,3-b]pyridin-3-ol (SMS21032-0212-01)

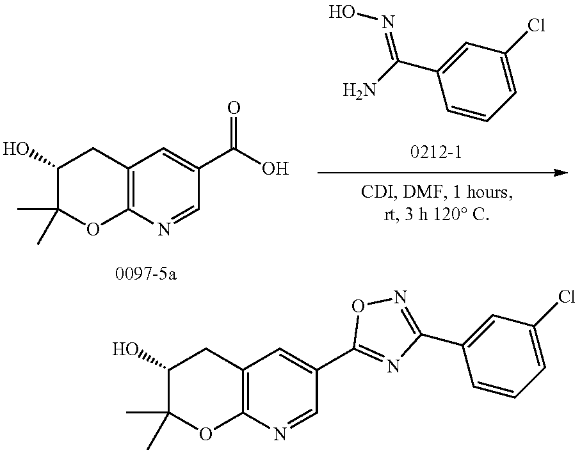

0097-5a

SMS21032-0212-01

(3R)-3-hydroxy-2,2-dimethyl-3,4-dihydropyrano[2,3-b]pyridine-6-carboxylic acid (80 mg, 358.38 umol) and then CDI (103.18 mg, 716.77 umol) were dissolved in DMF (1.5 mL). The mixture was stirred for 1 hr at 25° C. After that, 3-chloro-N'-hydroxy-benzamidine (326.07 mg, 716.77 umol) was added. The mixture was stirred for 3 hr at 120° C. After that, the reaction was tested by LC-MS. The result showed that the starting material fully reacted. Then the mixture was filtered. The crude product was purified by Pre-HPLC. The (3R)-6-[3-(3-chlorophenyl)-1,2,4-oxadiazol-5-yl]-2,2-dimethyl-3,4-dihydropyrano[2,3-b]pyridin-3-ol (50 mg, 139.75 umol, 38.99% yield) was obtained.

Agilent LCMS 21500-6120, Column: Waters X-Bridge C18 (50 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 98.42%, Rt=1.970 min; MS Found: 357.8 $[M+H]^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 99.85%, Rt=10.279 min.

$^1$H NMR (400 MHz, $CDCl_3$) δ 8.94 (d, J=2.3 Hz, 1H), 8.25-8.20 (m, 1H), 8.15 (t, J=1.7 Hz, 1H), 8.03 (dt, J=7.6, 1.3 Hz, 1H), 7.54-7.47 (m, 1H), 7.44 (t, J=7.8 Hz, 1H), 3.96 (q, J=5.2 Hz, 1H), 3.21 (dd, J=17.0, 4.8 Hz, 1H), 2.96 (dd, J=17.0, 5.7 Hz, 1H), 2.14 (d, J=5.8 Hz, 1H), 1.51 (s, 3H), 1.46 (s, 3H).

Example 32: The synthesis of (Z)—N'-hydroxyoxazole-2-carboximidamide (0213-1)

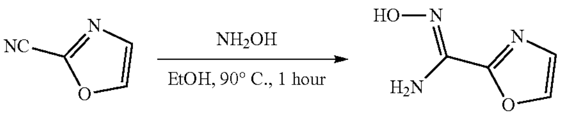

0213-1

A mixture of oxazole-2-carbonitrile (0.2 g, 2.13 mmol) in EtOH (5 mL) was added $NH_2OH$ (561.28 mg, 8.50 mmol, 50% purity). The mixture was stirred at 90° C. for 1 hour in a sealed tube. LCMS (NBK0071-52-P1-1) showed that the desired product was generated and the purity was 100%. The mixture was concentrated in vacuo. N'-hydroxyoxazole-2-carboxamidine (260 mg, 2.05 mmol, 96.22% yield, 100% purity) as a white solid was obtained.

The synthesis of (S)-2,2-dimethyl-6-(3-(oxazol-2-yl)-1,2,4-oxadiazol-5-yl)-3,4-dihydro-2H-pyrano[2,3-b]pyridin-3-ol (SMS21032-0213-01)

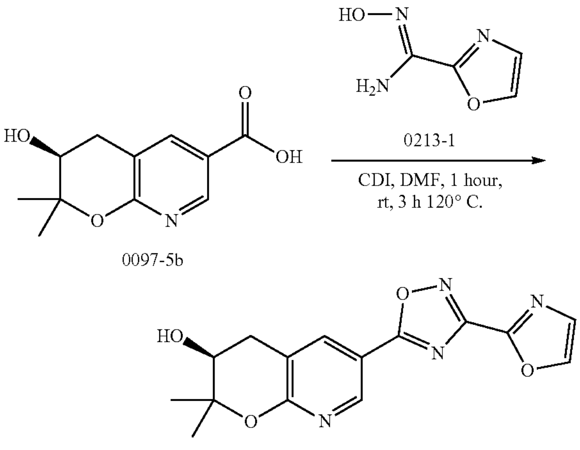

0097-5b

SMS21032-0213

A mixture of (3S)-3-hydroxy-2,2-dimethyl-3,4-dihydropyrano[2,3-b]pyridine-6-carboxylic acid (60 mg, 268.79 umol) in DMF (3 mL) was added di(imidazol-1-yl)methanone (87.17 mg, 537.57 umol). The mixture was stirred at 25° C. for 1 hour. Then N'-hydroxyoxazole-2-carboxamidine (47.83 mg, 376.30 umol) was added to the above mixture and stirred at 120° C. for 3 hours. LCMS showed that the desired product was generated. The product was purified by Prep. HPLC (base). (3S)-2,2-dimethyl-6-(3-oxazol-2-yl-1,2,4-oxadiazol-5-yl)-3,4-dihydropyrano[2,3-b] pyridin-3-ol (35 mg, 106.91 umol, 96% purity) as a white solid was obtained. Yield: 41.4%.

Agilent LCMS 290520-6120, Column: Waters X-Bridge C18 (150 mm*4.6 mm*3.5 m); Column Temperature: 40° C.; Flow Rate: 1.5 mL/min; Mobile Phase: from 95% [water+0.05FA] and 5% [$CH_3CN$] to 0% [water+0.05% FA] and 95% [$CH_3CN$] in 2 min, then under this condition for 4 min, finally changed to 95% [water+0.05FA] and 5% [$CH_3CN$] in 2 min and under this condition for 2 min, Purity: 100%, Rt=1.901 min; MS Found: 314.9 [M+H]$^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 96.35%, Rt=8.279 min $^1$H NMR (400 MHz, $CDCl_3$) δ 9.02 (d, J=2.1 Hz, 1H), 8.30 (d, J=1.1 Hz, 1H), 7.91 (s, 1H), 7.45 (s, 1H), 3.97 (s, 1H), 3.19 (dd, J=17.0, 4.7 Hz, 1H), 2.94 (dd, J=17.0, 5.8 Hz, 1H), 2.01 (s, 1H), 1.50 (s, 3H), 1.47 (s, 3H).

Example 33: The synthesis of (R)-2,2-dimethyl-6-(3-(pyrimidin-5-yl)-1,2,4-oxadiazol-5-yl)-3,4-dihydro-2H-pyrano[2,3-b]pyridin-3-ol (0214)

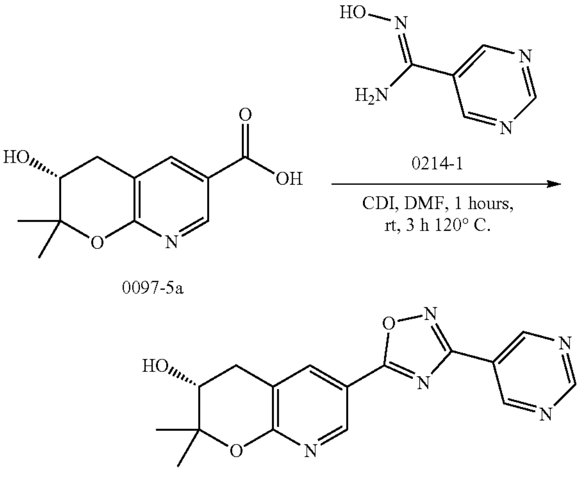

0097-5a

SMS21032-0214-01

(R)-3-hydroxy-2,2-dimethyl-3,4-dihydro-2H-pyrano[2,3-b]pyridine-6-carboxylic acid (80 mg, 446.39 umol) and CDI (128.52 mg, 892.78 umol) was dissolved in DMF (2 mL). The mixture was stirred for 1 hr at 25° C. N'-hydroxyoxazole-2-carboxamidine (113.47 mg, 892.78 umol) was added. The mixture was stirred for 3 hr at 120° C. After that, the reaction was tested by LC-MS. The result showed that the starting material was fully reacted and the target compound was formed.

The (3R)-2,2-dimethyl-6-(3-oxazol-2-yl-1,2,4-oxadiazol-5-yl)-3,4-dihydropyrano[2,3-b]pyridin-3-ol (35 mg, 111.36 umol, 24.95% yield) was purified by Pre-HPLC.

Agilent LCMS 21500-6120, Column: Waters X-Bridge C18 (50 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 98.85%, Rt=1.804 min; MS Found: 314.9 [M+H]$^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 98.58%, Rt=8.283 min.

Analysis of H-NMR: $^1H$ NMR (400 MHz, DMSO) δ 8.82 (d, J=2.4 Hz, 1H), 8.50 (d, J=0.7 Hz, 1H), 8.35-8.31 (m, 1H), 7.64 (d, J=0.7 Hz, 1H), 5.38 (d, J=4.1 Hz, 1H), 3.78 (dd, J=9.5, 4.8 Hz, 1H), 3.13 (dd, J=17.2, 4.6 Hz, 1H), 2.83 (dd, J=17.2, 6.1 Hz, 1H), 1.34 (s, 6H).

Example 34: The synthesis of (Z)-4-chloro-3-fluoro-N'-hydroxybenzimidamide (0215-1)

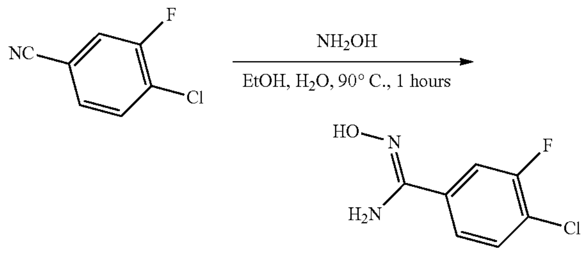

0215-1

4-chloro-3-fluoro-benzonitrile (200 mg, 1.29 mmol) was dissolved in EtOH (5 mL), and then $NH_2OH$ (339.73 mg, 5.14 mmol, 50% purity) was added. The mixture was stirred for 1 hr at 90° C. After that, the reaction was tested by LC-MS. The result showed that the raw material was disappeared. Then the mixture was filtered in vacuo. The crude product 4-chloro-3-fluoro-N'-hydroxy-benzamidine (230 mg, 1.16 mmol, 95% purity) was obtained. The product would be used to the next step reaction without any purification.

The synthesis of (S)-6-(3-(4-chloro-3-fluorophenyl)-1,2,4-oxadiazol-5-yl)-2,2-dimethyl-3,4-dihydro-2H-pyrano[2,3-b]pyridin-3-ol (0215-1)

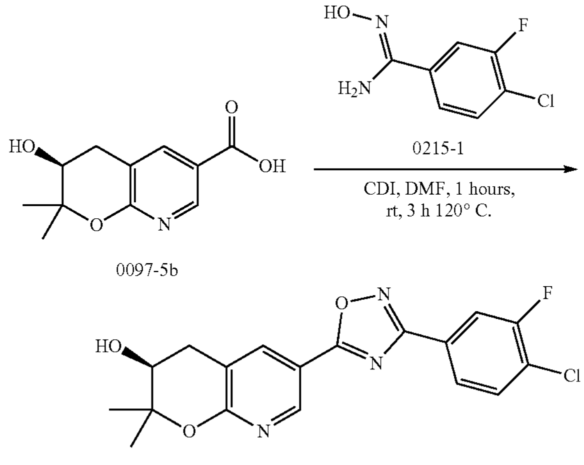

0215-1

0097-5b

SMS21032-0215-1

(3 S)-3-hydroxy-2,2-dimethyl-3,4-dihydropyrano[2,3-b]pyridine-6-carboxylic acid (60 mg, 268.79 umol) and CDI (38.69 mg, 268.79 umol) was dissolved in DMF (1.5 mL). The mixture was stirred for 1 hr at 25° C. And then 4-chloro-3-fluoro-N'-hydroxy-benzamidine (60.83 mg, 322.54 umol) was added. The mixture was stirred for 3 hr at 120° C. After that, the reaction was tested by LC-MS. The result showed that the starting material was fully reacted. Then the mixture was filtered in vacuo. The crude product was purified by Pre-HPLC. The (3S)-6-[3-(4-chloro-3-fluoro-phenyl)-1,2,4-oxadiazol-5-yl]-2,2-dimethyl-3,4-dihydropyrano[2,3-b]pyridin-3-ol (25 mg, 66.53 umol, 24.75% yield) was obtained.

Agilent LCMS 21500-6120, Column: Waters X-Bridge C18 (50 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 100%, Rt=2.839 min; MS Found: 375.8 $[M+H]^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 97.68%, Rt=10.378 min.

$^1H$ NMR (400 MHz, $CDCl_3$) δ 8.92 (d, J=2.3 Hz, 1H), 8.24-8.17 (m, 1H), 7.93 (dd, J=9.5, 1.8 Hz, 1H), 7.91-7.87 (m, 1H), 7.56-7.51 (m, 1H), 3.97 (dd, J=10.8, 5.6 Hz, 1H), 3.21 (dd, J=17.0, 4.8 Hz, 1H), 2.96 (dd, J=17.0, 5.7 Hz, 1H), 2.14 (d, J=6.2 Hz, 1H), 1.51 (s, 3H), 1.46 (s, 3H).

Example 35: The synthesis of (Z)-4-chloro-3-fluoro-N'-hydroxybenzimidamide (0216-1)

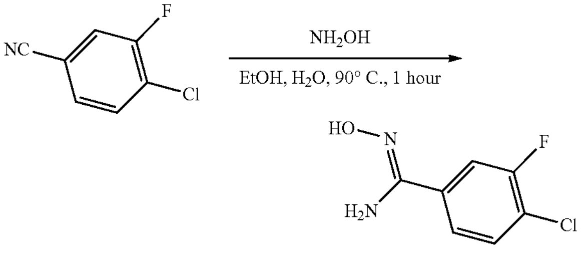

0216-1

4-chloro-3-fluoro-benzonitrile (200 mg, 1.29 mmol) was dissolved in EtOH (5 mL). $NH_2OH$ (339.73 mg, 5.14 mmol, 50% purity) was added. The mixture was stirred for 1 hr at 90° C. After that, the reaction was tested by LC-MS. The result showed that the starting material was fully reacted. Then the mixture was filtered and the crude product 4-chloro-3-fluoro-N'-hydroxy-benzamidine (230 mg, 1.16 mmol, 95% purity) was obtained. The product was used to the next step reaction without any purification.

The synthesis of(S)-6-(3-(4-chloro-3-fluorophenyl)-1,2,4-oxadiazol-5-yl)-2,2-dimethyl-3,4-dihydro-2H-pyrano[2,3-b]pyridin-3-ol (SMS21032-0216-01)

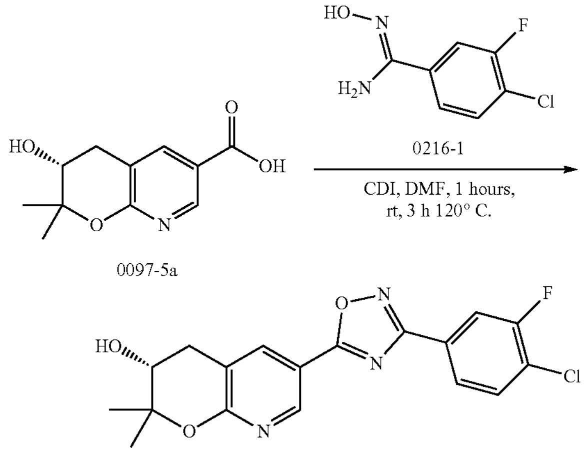

0097-5a

SMS21032-0216-1

(3 S)-3-hydroxy-2,2-dimethyl-3,4-dihydropyrano[2,3-b] pyridine-6-carboxylic acid (60 mg, 268.79 umol) and CDI (38.69 mg, 268.79 umol) was dissolved in DMF (1.5 mL). The mixture was stirred for 1 hr at 25° C. And then 4-chloro-3-fluoro-N'-hydroxy-benzamidine (60.83 mg, 322.54 umol) was added. The mixture was stirred for 3 hr at 120° C. After that, the reaction was tested by LC-MS. The result showed that the starting material was fully reacted. Then the mixture was concentrated and the crude product was purified by Pre-HPLC to afford (3S)-6-[3-(4-chloro-3-fluoro-phenyl)-1,2,4-oxadiazol-5-yl]-2,2-dimethyl-3,4-dihydropyrano [2,3-b]pyridin-3-ol (25 mg, 66.53 umol, 24.75% yield).

Agilent LCMS 21500-6120, Column: Waters X-Bridge C18 (50 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 100%, Rt=2.839 min; MS Found: 375.8 $[M+H]^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 96.39%, Rt=10.364 min.

$^1H$ NMR (400 MHz, $CDCl_3$) δ8.92 (d, J=2.3 Hz, 1H), 8.24-8.17 (m, 1H), 7.93 (dd, J=9.5, 1.8 Hz, 1H), 7.91-7.87 (m, 1H), 7.56-7.51 (m, 1H), 3.97 (dd, J=10.8, 5.6 Hz, 1H), 3.21 (dd, J=17.0, 4.8 Hz, 1H), 2.96 (dd, J=17.0, 5.7 Hz, 1H), 2.14 (d, J=6.2 Hz, 1H), 1.51 (s, 3H), 1.46 (s, 3H).

Example 36: The synthesis of (Z)-4-chloro-N'-hydroxy-3-methylbenzimidamide (0217-1)

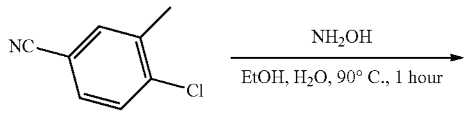

-continued

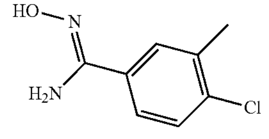

0217-1

A mixture of 4-chloro-3-methyl-benzonitrile (200.0 mg, 1.32 mmol) in EtOH (5 mL) was added $NH_2OH$ (348.62 mg, 5.28 mmol, 480.19 uL, 50% purity). The mixture was stirred at 90° C. for 1 hour. LCMS showed that the desired product was generated and one main peak was detected. The mixture was concentrated in vacuo. 4-chloro-N'-hydroxy-3-methyl-benzamidine (240.0 mg, 1.27 mmol, 98% purity) as a white solid was obtained. The synthesis of(S)-6-(3-(3-chlorophenyl)-1,2,4-oxadiazol-5-yl)-2,2-dimethyl-3,4-dihydro-2H-pyrano[2,3-b]pyridin-3-ol (SMS21032-0217-01)

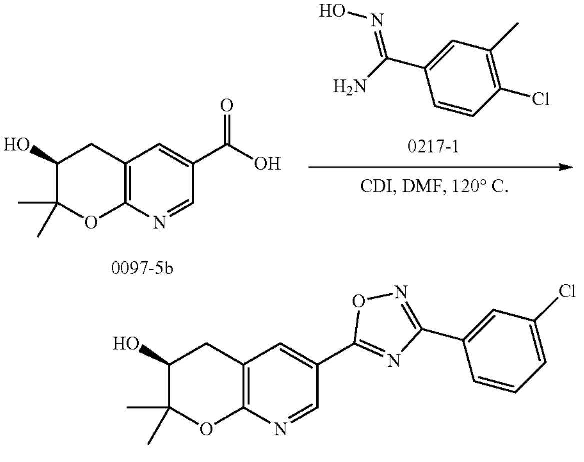

0097-5b

SMS21032-0217-1

A mixture of (3S)-3-hydroxy-2,2-dimethyl-3,4-dihydropyrano[2,3-b]pyridine-6-carboxylic acid (40.0 mg, 179.19 umol) in DMF (2 mL) was added di(imidazol-1-yl)methanone (58.11 mg, 358.38 umol). The mixture was stirred at 25° C. for 1 hour. Then 4-chloro-N'-hydroxy-3-methyl-benzamidine (39.70 mg, 215.03 umol) was added to the mixture and stirred at 120° C. for 3 hours. LCMS (NBK0071-39-P1-1) showed that the desired product was generated. The mixture was combined with NBK0071-034. The product was purified by Prep.HPLC(base).

The eluent was dried by lyophilization. (3S)-6-[3-(4-chloro-3-methyl-phenyl)-1,2,4-oxadiazol-5-yl]-2,2-dimethyl-3,4-dihydropyrano[2,3-b]pyridin-3-ol (34 mg, 90.53 umol, 99% purity) as a white solid was obtained. QC (NBK0071-39-P1-2) showed that it was qualified to deliver. Yield: 38.3%.

Agilent LCMS 200520-6120, Column: Waters X-Bridge C18 (150 mm*4.6 mm*3.5 m); Column Temperature: 40° C.; Flow Rate: 1.5 mL/min; Mobile Phase: from 95% [water+0.05FA] and 5% [$CH_3CN$] to 0% [water+0.05% FA] and 95% [$CH_3CN$] in 2 min, then under this condition for 4 min, finally changed to 95% [water+0.05FA] and 5% [$CH_3CN$] in 2 min and under this condition for 2 min, Purity: 100%, Rt=2.803 min; MS Found: 372.8 $[M+H]^+$.

Agilent HPLC 1260-03, Column: Agilent Eclipse C18 Plus 4.6×100 mm 3.5 um; Column Temperature: 40° C.;

Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 98.54%, Rt=10.702 min.

$^1$H NMR (400 MHz, $CDCl_3$) δ 8.92 (d, J=2.3 Hz, 1H), 8.24-8.18 (m, 1H), 8.01 (d, J=1.4 Hz, 1H), 7.90 (dd, J=8.3, 1.9 Hz, 1H), 7.46 (d, J=8.3 Hz, 1H), 3.96 (q, J=5.3 Hz, 1H), 3.20 (dd, J=17.0, 4.7 Hz, 1H), 2.96 (dd, J=17.0, 5.7 Hz, 1H), 2.46 (s, 3H), 2.15 (d, J=6.0 Hz, 1H), 1.51 (s, 3H), 1.46 (s, 3H). ESI(M+H)+=372.8.

Example 37: The synthesis of (R)-6-(3-(3-chlorophenyl)-1,2,4-oxadiazol-5-yl)-2,2-dimethyl-3,4-dihydro-2H-pyrano[2,3-b]pyridin-3-ol (SMS21032-0218-01)

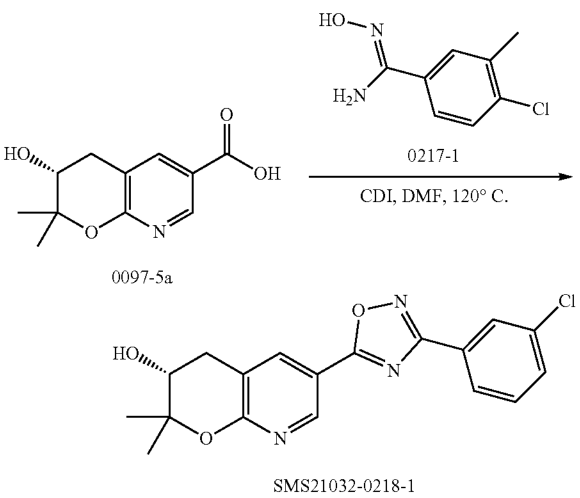

A mixture of (3R)-3-hydroxy-2,2-dimethyl-3,4-dihydropyrano[2,3-b]pyridine-6-carboxylic acid (60.00 mg, 268.79 umol) in DMF (3 mL) was added di(imidazol-1-yl)methanone (87.17 mg, 537.57 umol). The mixture was stirred at 25° C. for 1 hour. Then 4-chloro-N'-hydroxy-3-methylbenzamidine (59.55 mg, 322.54 umol) was added to the mixture and stirred at 120° C. for 3 hours. LCMS (NBK0071-40-P1-1) showed that the desired product was generated. The product was purified by Prep.HPLC(base). The eluent was dried by lyophilization. (3R)-6-[3-(4-chloro-3-methyl-phenyl)-1,2,4-oxadiazol-5-yl]-2,2-dimethyl-3,4-dihydropyrano[2,3-b]pyridin-3-ol (33 mg, 87.87 umol, 32.69% yield, 99% purity) as a white solid was obtained.

Yield: 32.69% Agilent LCMS 200520-6120, Column: Waters X-Bridge C18 (150 mm*4.6 mm*3.5 m); Column Temperature: 40° C.; Flow Rate: 1.5 mL/min; Mobile Phase: from 95% [water+0.05FA] and 5% [$CH_3CN$] to 0% [water+0.05% FA] and 95% [$CH_3CN$] in 2 min, then under this condition for 4 min, finally changed to 95% [water+0.05FA] and 5% [$CH_3CN$] in 2 min and under this condition for 2 min, Purity: 100%, Rt=2.802 min; MS Found: 373.8 $[M+H]^+$.

Agilent HPLC 1260-03, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 99.22%, Rt=10.701 min.

$^1$H NMR (400 MHz, $CDCl_3$) δ 8.92 (d, J=2.1 Hz, 1H), 8.21 (d, J=0.9 Hz, 1H), 8.00 (s, 1H), 7.89 (dd, J=8.3, 1.7 Hz, 1H), 7.46 (d, J=8.3 Hz, 1H), 4.01-3.90 (m, 1H), 3.20 (dd, J=17.0, 4.7 Hz, 1H), 2.96 (dd, J=17.0, 5.6 Hz, 1H), 2.46 (s, 3H), 2.18 (d, J=6.3 Hz, 1H), 1.51 (s, 3H), 1.46 (s, 3H). ESI (M+H)+=372.8.

Example 38: The synthesis of (R)-6-(3-(3-fluorophenyl)-1,2,4-oxadiazol-5-yl)-2,2-dimethyl-3,4-dihydro-2H-pyrano[2,3-b]pyridin-3-ol (SMS21032-0259)

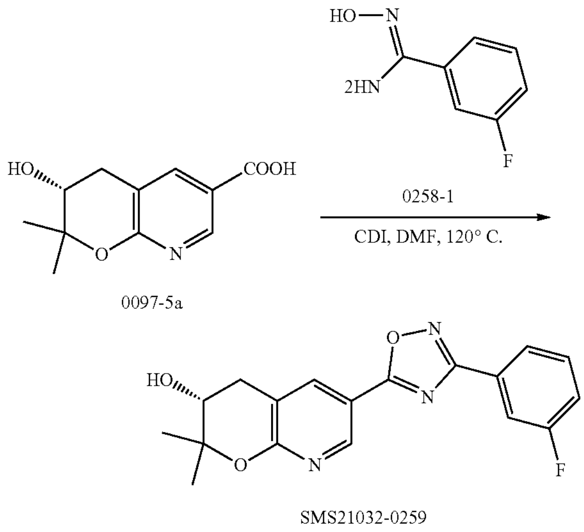

A mixture of (3R)-3-hydroxy-2,2-dimethyl-3,4-dihydropyrano[2,3-b]pyridine-6-carboxylic acid (80 mg, 358.38 umol) in DMF (3 mL) was added N, N'-carbonyldiimidazole (116.12 mg, 716.77 umol). The mixture was stirred at 25° C. for 1 hour. Then 3-fluoro-N'-hydroxy-benzamidine (55.24 mg, 358.38 umol) was added to the above mixture and stirred at 120° C. for 4 hours. LCMS (NBK0071-184-P1-1) showed that the desired product was generated. The product was purified by Prep HPLC (basic). (3R)-6-[3-(3-fluorophenyl)-1,2,4-oxadiazol-5-yl]-2,2-dimethyl-3,4-dihydropyrano[2,3-b]pyridin-3-ol (23 mg, 67.38 umol) as a white solid was obtained.

Agilent LCMS 6120, Column: Waters X-Bridge C18 (150 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 99.10%, Rt=2.406 min; MS Found: 341.9$[M+H]^+$.

Agilent HPLC 1260, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 97.65%, Rt=9.849 min.

$^1H$ NMR (400 MHz, $CDCl_3$) δ 8.96 (d, J=2.2 Hz, 1H), 8.25-8.20 (m, 1H), 7.98-7.92 (m, 1H), 7.85 (ddd, J=9.5, 2.5, 1.5 Hz, 1H), 7.48 (td, J=8.0, 5.7 Hz, 1H), 7.23 (tdd, J=8.4, 2.6, 0.9 Hz, 1H), 3.97 (dd, J=5.6, 4.9 Hz, 1H), 3.21 (dd, J=17.0, 4.8 Hz, 1H), 2.96 (dd, J=17.0, 5.7 Hz, 1H), 1.51 (s, 3H), 1.47 (s, 3H). $^{19}$FNMR (376 MHz, CDCl3) δ-111.86 (s).

Example 39: The synthesis of (Z)-3,5-dichloro-N'-hydroxybenzimidamide (0260-1)

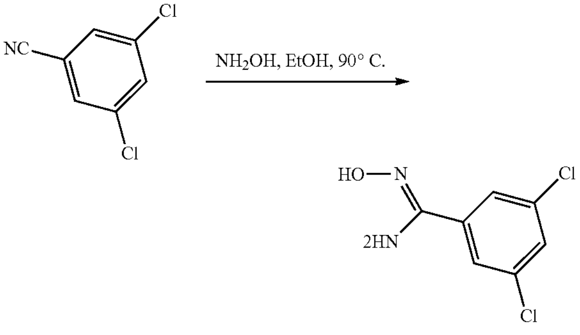

0260-1

A mixture of 3,5-dichlorobenzonitrile (0.5 g, 2.91 mmol, 882.61 uL) in EtOH (10 mL) was added hydroxylamine (768.09 mg, 11.63 mmol). The mixture was stirred at 90° C. for 2 hours. LCMS (NBK0071-180-P1-1) showed that the desired product was generated. The mixture was concentrated in vacuo and the product was dried by lyophilization. 3,5-dichloro-N'-hydroxy-benzamidine (590 mg, 2.88 mmol) as a white solid was obtained. The synthesis of(S)-6-(3-(3, 5-dichlorophenyl)-1,2,4-oxadiazol-5-yl)-2,2-dimethyl-3,4-dihydro-2H-pyrano[2,3-b]pyridin-3-ol (SMS21032-0260-01)

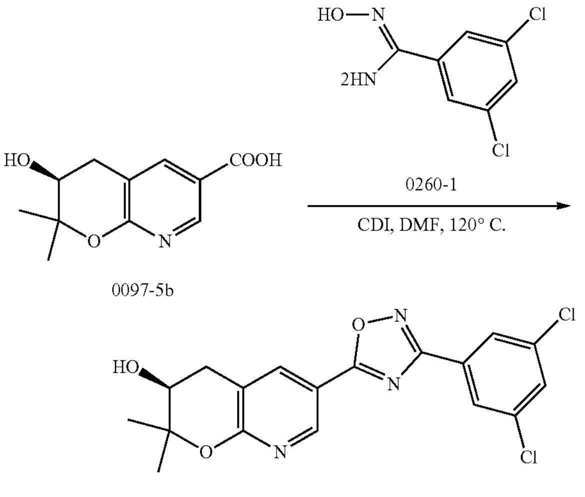

0260-1

0097-5b

SMS21032-0260

A mixture of (3S)-3-hydroxy-2,2-dimethyl-3,4-dihydro-pyrano[2,3-b]pyridine-6-carboxylic acid (80 mg, 358.38 umol) in DMF (3 mL) was added N, N'-carbonyldiimidazole (116.12 mg, 716.77 umol). The mixture was stirred at 25° C. for 1 hour. Then 3,5-dichloro-N'-hydroxy-benzamidine (110.22 mg, 537.57 umol) was added to the above mixture and stirred at 120° C. for 4 hours. LCMS (NBK0071-185-P1-1) showed that the desired product was generated.

The product was purified by Prep HPLC (basic). (3S)-6-[3-(3,5-dichlorophenyl)-1,2,4-oxadiazol-5-yl]-2,2-dimethyl-3,4-dihydropyrano[2,3-b]pyridin-3-ol (9 mg, 22.95 umol) as a white solid was obtained.

Agilent LCMS 6120, Column: Waters X-Bridge C18 (150 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 98.79%, Rt=2.874 min; MS Found: 393.8M+H]$^+$.

Agilent HPLC 1260, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 96.01%, Rt=11.281 min.

$^1H$ NMR (400 MHz, $CDCl_3$) δ 8.94 (d, J=2.3 Hz, 1H), 8.24-8.19 (m, 1H), 8.05 (d, J=1.9 Hz, 2H), 7.51 (t, J=1.9 Hz, 1H), 3.97 (d, J=5.1 Hz, 1H), 3.21 (dd, J=17.0, 4.8 Hz, 1H), 2.96 (dd, J=17.0, 5.7 Hz, 1H), 2.07 (d, J=6.2 Hz, 1H), 1.51 (s, 3H), 1.46 (s, 3H).

Example 40: The synthesis of (R)-6-(3-(3,5-dichlorophenyl)-1,2,4-oxadiazol-5-yl)-2,2-dimethyl-3,4-dihydro-2H-pyrano[2,3-b]pyridin-3-ol (SMS21032-0261-01)

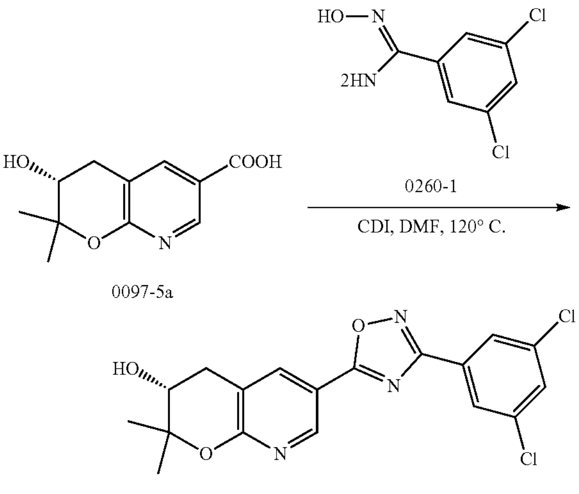

0260-1

0097-5a

SMS21032-0261

A mixture of (3R)-3-hydroxy-2,2-dimethyl-3,4-dihydro-pyrano[2,3-b]pyridine-6-carboxylic acid (80 mg, 358.38 umol) in DMF (3 mL) was added N, N'-carbonyldiimidazole (116.12 mg, 716.77 umol). The mixture was stirred at 25° C. for 1 hour. Then 3,5-dichloro-N'-hydroxy-benzamidine (110.22 mg, 537.57 umol) was added to the mixture and stirred at 120° C. for 4 hours. LCMS (NBK0071-186-P1-1)

showed that the desired product was generated. The product was purified by Prep HPLC (basic). (3R)-6-[3-(3,5-dichlorophenyl)-1,2,4-oxadiazol-5-yl]-2,2-dimethyl-3,4-dihydropyrano[2,3-b]pyridin-3-ol (32 mg, 81.58 umol) as a white solid was obtained. QC showed that it was qualified to delivery.

Agilent LCMS 6120, Column: Waters X-Bridge C18 (150 mm*4.6 mm*3.5 m); Column Temperature: 40° C.; Flow Rate: 1.5 mL/min; Mobile Phase: from 95% [water+10 mM $NH_4HCO_3$] and 5% [$CH_3CN$] to 0% [water+10 mM $NH_4HCO_3$] and 95% [$CH_3CN$] in 2 min, then under this condition for 4 min, finally changed to 95% [water+10 mM $NH_4HCO_3$] and 5% [$CH_3CN$] in 2 min and under this condition for 2 min, Purity: 97.45%, Rt=2.877 min; MS Found: 393.8$[M+H]^+$.

Agilent HPLC 1260, Column: Agilent Eclipse C18 Plus 4.6×100 mm 3.5 um; Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 14 min, then under this condition for 8 min, finally changed to 95% [water+10 mM $NH_4HCO_3$] and 5% [$CH_3CN$] in 0.1 min and under this condition for 6 min, Purity: 96.92%, Rt=11.233 min.

$^1H$ NMR (400 MHz, $CDCl_3$) δ 8.89 (d, J=2.3 Hz, 1H), 8.23-8.18 (m, 1H), 8.02 (d, J=1.9 Hz, 2H), 7.50 (t, J=1.9 Hz, 1H), 3.97 (t, J=5.0 Hz, 1H), 3.21 (dd, J=17.0, 4.7 Hz, 1H), 2.97 (dd, J=17.0, 5.5 Hz, 1H), 2.34 (s, 1H), 1.52 (s, 3H), 1.46 (s, 3H).

Other examples not specifically described above were made analogously.

Using a combined systems biology and experimental approach, we have previously identified homeodomain interacting protein kinase 2 (HIPK2) as a critical regulator of multiple pro-fibrosis pathways including TGF-β1/Smad3 pathway. HIPK2 regulates the pathway by physical association with Smad3, which thereby modulates its activity.

Knockdown of HIPK2 in human primary tubular cells suppresses activation of the TGF-β1/Smad3 pathway induced by TGF-β1. In vivo, HIPK2 knockout inhibits TGF-β1/Smad3 activity and kidney fibrosis in both HIV1-transgenic mice (Tg26) and mice with unilateral ureteral obstruction (UUO). Suppression of TGF-β1/Smad3 pathway through inhibition of HIPK2, therefore provides an approach to anti-fibrosis therapy for kidney disease.

HIPK2 inhibitors have not been well developed and are not commercially available. Recently Cozza et al [PLoS One, 9: e89176, 2014] described a selective HIPK2 inhibitor that competes for the ATP binding in the kinase domain. However, since HIPK2 regulates multiple signaling pathways, including regulation of p53, there is a concern that broad inhibition of HIPK2 may not be beneficial in all cellular contexts. Here we describe compounds that may inhibit TGF-β1/Smad3 pathway through the interruption of HIPK2-Smad3 protein-protein interaction without significant inhibition of HIPK2 kinase activity or inhibition of p53 activation. In the tests shown below, examples of compounds of the invention inhibited the pro-fibrosis pathway in vitro in cultured human renal tubular epithelial cells (RTEC) and in vivo in murine models of kidney fibrosis (Tg26 and UUO mice).

HEK 293T (293T) cells (ATCC) are cultured in Dulbecco's Modified Eagle's medium (Invitrogen) containing 10% fetal bovine serum (FBS), 0.5% penicillin and streptomycin at 37° C. and 5% $CO_2$ humidified environment. Human primary tubular cells (PromoCell GmbH, Heidelberg, Germany) are cultured in Renal Epithelial Cell Growth Medium-2 (Promocell GmbH) with supplements according to manufacturer's protocol. Human primary renal tubular epithelial cells with <5 passages are used for all studies. For HIV infection of hRTECs, pNL4-3:ΔG/P-EGFP, a gag/pol-deleted HIV-1 construct that contains EGFP in the gag open reading frame, and pHR-IRES-EGFP, a control EGFP construct, are used to generate the VSV-G pseudotyped virus. Cells are infected with HIV pseudotyped virus or control virus for 2 days before the treatment with test compound.

4× Smad binding element-driven firefly luciferase (SBE4-Luc) plasmid and Renilla luciferase reporter plasmid (pRL) are available commercially. Active domain deleted HIPK2 was previously described by Jin et al. [Nat Med, 18: 580-588]. The $His_6$-HIPK2 construct is generated by PCR amplification of coding region using plasmid containing human HIPK2 gene (GeneCopoeia™) as the template.

293T cells seeded in 12-well plate (~60% confluence) are co-transfected with SBE4-Luc (0.5 g) and pRL plasmids (0.2 g) using the PolyJet transfection kit according to manufacturer's instructions (SignaGen Laboratories, MD). Forty-eight hours post-transfection cells are treated with assigned concentrations of test compound together with or without 10 ng/ml TGF-β1 for 16 hours. Luciferase activities are measured using the Dual-Luciferase Reporter Assay kit (Promega, #E1910). Data are expressed as the ratio of firefly luciferase activity over renilla luciferase activity. For HIPK2 dominant negative experiment, together with SBE4-firefly luciferase and pRL (renilla luciferase) plasmids, either pcDNA 3.1 empty vector (0.5 g) or HIPK2 KD plasmid (0.5 g) are co-transfected into 293T cells. 48 hours after transfection, luciferase activities are measured.

For the data in Table 1, the Bight-Glo™ Luciferase Assay System from Promega was used with TGF/SMAD Signaling Pathway SBE Reporter—HEK293 Cell Line from BPSbioscience. On day 1 SBE reporter-HEK293 cells were seeded at a density of 25,000 cells per well into a white clear-bottom 96-well microplate in 100 μl of growth medium without geneticin. The plate was incubated at 37° C. in a $CO_2$ incubator for 24 hrs. The wells were renewed with 60 μL assay medium and treated with test compounds by adding 5 μL of compounds in medium. The concentration of test compound in medium is adjusted so that 5 μL will provide the desired molarity of the solution. For example, if the desired test concentration is 30 M, then 5 μL of 660 μM compound is added. After 4 hours, TGFβ was added to 10 ng/mL. The plate was incubated at 37° C. in a $CO_2$ incubator overnight (18 hours). One hour prior to assay all medium was replaced. The luciferase assay was run using ONE-Step™ Luciferase Assay System by adding 100 al of ONE-Step™ Luciferase reagent per well, rocking at room temperature for ~15 to 30 minutes and measuring luminescence using a luminometer. The signals were normalized to percentage inhibition, with non-TGF treated cells as 100% inhibition, and the data were processed by Graphpad Prism.

Activity of compounds of the invention was confirmed in vivo. Two chronic kidney disease models were employed: (1) Tg26 mice, a model of HIV-associated nephropathy, and (2) Col4a3-null mice, a model of Alport syndrome. Both CKD models are characterized by advanced glomerulosclerosis and tubulointerstitial fibrosis, leading to kidney failure and death approximately between 12 and 20 weeks of age.

Tg26 mice of FVB/N genetic background bearing a defective HIV-1 provirus lacking gag-pol have been described by Feng et al. [*J Am Soc Nephrol* 2009; 20: 2138-2146]. Six-week old heterozygous Tg26 mice are used. Wildtype littermates are used as controls. Mice in the treatment group receive test compound dissolved in 20% NMP, 60% PEG400, and 20% $H_2O$ by oral gavage at a dose of 30, 60, or 90 mg/kg body weight per day. Mice in the control group receive the same volume of vehicle. The mice are treated for a total of 4 weeks and sacrificed at age of 10 weeks. Four-week treatment of Tg26 mice with the compound of Example 13 resulted in improved survival (64% survival in vehicle group [n=25 mice] vs. 100% survival in the group treated with Example 13 [n=20 mice]; Hazard ratio=7.2 in comparing vehicle vs. treatment with Example 13; p-value: 0.003 by Log-rank Mantel-Cox test); ~65% reduction in average fold change in urinary albumin-to-creatinine ratio (average fold change of 1.057 from week 0 to week 4 in vehicle group [n=9 mice] vs. 0.352 in Example 13 group [n=8 mice]; p-value=0.0001 by Welch's t-test), and ~43% reduction in renal fibrosis area (average % area of 4.492 vehicle group [n=9 mice] vs. 2.540 in Example 13 group [n=8 mice], p-value=0.008). In another trial, 5- to 6-week old Tg26 mice were treated with Example 13 (90 mg/kg daily, PO) or vehicle for 4 weeks: 38% (8/21 mice) died of kidney failure in the control group within the experimental duration; 0% died in the HIPK2i-174 group (0/18 mice). The comparison of urinary albumin-to-creatinine ratio (UCAR), as a measure of glomerular function, showed ~16% increase from baseline values in the vehicle group (fold change: 1.16±0.47, n=15), but a ~57% reduction in the HIPK2i-174 group (fold change: 0.43±0.28, n=17, p=0.0001 by unpaired, 2-tailed t-test with Welch's correction). [Because of significant inter-variability of baseline UACR in Tg26 mice at 5-6 weeks of age, the therapeutic effect is calculated based on fold change to baseline for each mouse.] The comparison of kidney fibrosis, assessed by picrosirius red histological staining, showed ~37% reduction in fibrosis in the group treated with example 13 (2.8±1.2%, n=18, p=0.008) in comparison to vehicle group (4.44±1.2%, n=16).

Three-week old Col4a3-deficient mice were treated with Example 13 (60 mg/kg daily, PO) or vehicle for 6 weeks. The median survival in vehicle group was 56 days, which was increased to 68 days in the treated group (21% increase). The comparison of urinary albumin-to-creatinine ratio (UCAR) showed ~45% reduction in treated group (73.9±34.9 vs. 41.4±14.2 mg/mg) after 6 weeks of treatment. The comparison of kidney fibrosis, assessed by picrosirius red histological staining, showed ~51% reduction in fibrosis in the treated group (13.7±6.3%, n=9, p=0.0001) in comparison to vehicle group (28.3±4.4%, n=8).

In view of the mechanism of action of the compounds of the invention, the artisan will recognize that the treatment of fibrotic diseases in organs other than kidney would be similarly successful. Compounds of the invention are currently under trial in models for treating fibrosis of lung, heart, and liver.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A compound of formula I

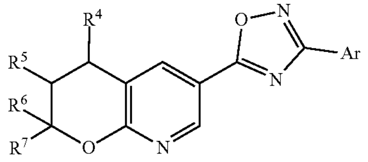

I wherein

Ar is (a) phenyl substituted at the meta and/or para positions with one or more substituents chosen independently from hydrogen, —$(C_1\text{-}C_8)$hydrocarbyl, OH, —$O(C_1\text{-}C_8)$hydrocarbyl, halogen, nitro, amino, $(C_1\text{-}C_3)$alkylamino, $(C_1\text{-}C_3)$dialkylamino, $(C_1\text{-}C_3)$acylamino, $(C_1\text{-}C_3)$alkylsulfonyl, $(C_1\text{-}C_3)$haloalkyl, $(C_1\text{-}C_3)$haloalkoxy, 5- or 6-membered heterocyclyl, and —$B(OH)_2$; or (b) 5-membered heteroaryl chosen from thiophene, pyrazole oxazole, and thiazole, said thiophene, pyrazole, oxazole, or thiazole substituted with one substituent chosen from hydrogen, —$(C_1\text{-}C_3)$alkyl, OH, —$O(C_1\text{-}C_3)$alkyl, halogen, amino, $(C_1\text{-}C_3)$alkylamino, $(C_1\text{-}C_3)$dialkylamino, $(C_1\text{-}C_3)$haloalkyl, and $(C_1\text{-}C_3)$haloalkoxy;

$R^4$ is chosen from hydrogen, hydroxy, $(C_1\text{-}C_3)$alkyl, $(C_1\text{-}C_3)$alkoxy, amino, $(C_1\text{-}C_3)$alkylamino, and $(C_1\text{-}C_3)$dialkylamino;

$R^5$ is chosen from hydrogen, hydroxy, $(C_1\text{-}C_3)$alkyl, $(C_1\text{-}C_3)$alkoxy, amino, $(C_1\text{-}C_3)$alkylamino, and $(C_1\text{-}C_3)$dialkylamino;

$R^6$ is chosen from hydrogen and $(C_1\text{-}C_6)$hydrocarbyl; and $R^7$ is chosen from hydrogen and $(C_1\text{-}C_3)$alkyl;

with the proviso that not all of $R^4$, $R^5$, $R^6$, and $R^7$ are hydrogen.

2. A compound according to claim 1 wherein Ar is phenyl.

3. A compound according to claim 2 wherein phenyl is para-substituted with a substituent chosen from bromo, chloro, fluoro, fluoromethyl, difluoromethyl, trifluoromethyl, and methyl.

4. A compound according to claim 1 wherein Ar is chosen from thiophene, pyrazole, oxazole, and thiazole.

5. A compound according to claim 4 wherein Ar is unsubstituted or substituted with a substituent chosen from —$(C_1\text{-}C_3)$hydrocarbyl, bromo, chloro, fluoro, fluoromethyl, difluoromethyl, and trifluoromethyl.

6. A compound according to claim 1 wherein $R^4$ is chosen from hydrogen, hydroxy and amino.

7. A compound according to claim 1 wherein $R^5$ is chosen from hydrogen, hydroxy, methoxy, and amino.

8. A compound according to claim 1 wherein $R^6$ and $R^7$ are independently chosen from hydrogen and methyl.

9. A compound according to claim 8 wherein $R^6$ and $R^7$ are methyl and one of $R^4$ and $R^5$ is hydroxyl.

10. A compound according to claim 1 chosen from:

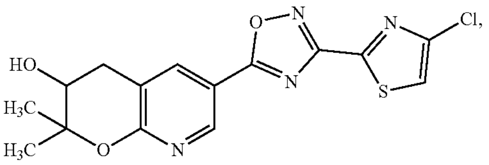

-continued

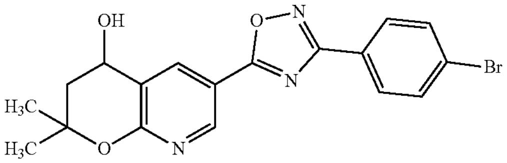

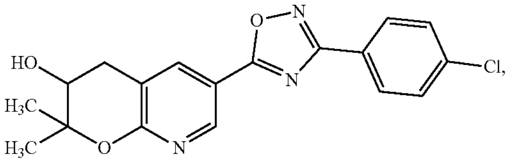

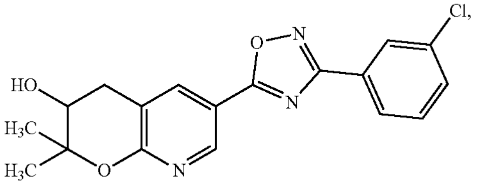

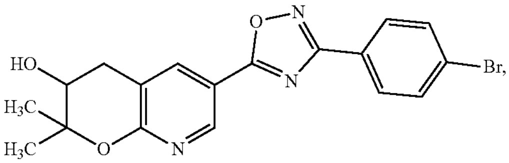

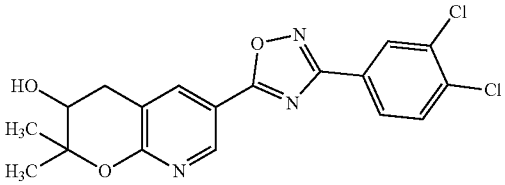

-continued

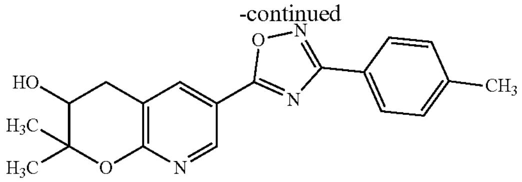

and

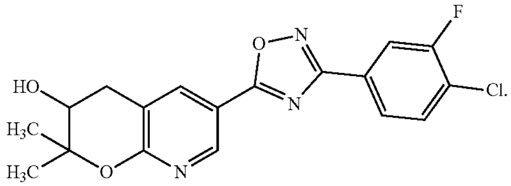

11. A compound according to claim 8 wherein Ar is thiazol-2-yl substituted at 3- or 4-with chloro or methyl.

12. A pharmaceutical composition comprising a pharmaceutically acceptable carrier and a compound according to claim 1.

13. A method for inhibiting the interaction of homeodomain interacting protein kinase 2 (HIPK2) with Smad3, said method comprising bringing HIPK2 into contact with a compound according to claim 1.

14. A method for inhibiting Smad3 activation, said method comprising bringing Smad3 into contact with a compound according to claim 1.

15. An in vitro method according to claim 13.

16. An in vivo method according to claim 13.

17. An in vitro or in vivo method according to claim 14.

18. A method for treating a fibrotic disease comprising administering a compound according to claim 1 to a subject suffering from renal fibrosis, cardiac fibrosis, hepatic fibrosis, or pulmonary fibrosis.

* * * * *